United States Patent
Arroyo et al.

(10) Patent No.: US 9,181,262 B2
(45) Date of Patent: *Nov. 10, 2015

(54) CRYSTALLINE FORMS OF A DIPEPTIDYL PEPTIDASE-IV INHIBITORS

(71) Applicants: Merck Sharp & Dohme Corp, Rahway, NJ (US); Merck Sharp & Dohme Ltd., Hoddesdon (GB)

(72) Inventors: Itzia Z. Arroyo, Union, NJ (US); Davida Krueger, Brooklyn, NY (US); Ping Chen, Edison, NJ (US); Aaron J. Moment, Scotch Plains, NJ (US); Tesfaye Biftu, Freehold, NJ (US); Faye Sheen, Hoddesdon (GB); Yanfeng Zhang, Panan (CN)

(73) Assignees: Merck Sharp & Dohme Corp, Rahway, NJ (US); Merck Sharp & Dohme Ltd., Hoddesdon (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/507,001

(22) Filed: Oct. 6, 2014

(65) Prior Publication Data

US 2015/0099891 A1   Apr. 9, 2015

Related U.S. Application Data

(63) Continuation of application No. 14/118,998, filed as application No. PCT/US2012/043922 on Jun. 25, 2012, now Pat. No. 8,895,603.

(60) Provisional application No. 61/502,497, filed on Jun. 29, 2011.

(51) Int. Cl.
| | |
|---|---|
| C07D 487/04 | (2006.01) |
| A61K 31/4162 | (2006.01) |
| A61K 31/4439 | (2006.01) |
| A61K 31/4985 | (2006.01) |
| A61K 31/513 | (2006.01) |

(52) U.S. Cl.
CPC .......... *C07D 487/04* (2013.01); *A61K 31/4439* (2013.01); *A61K 31/4985* (2013.01); *A61K 31/513* (2013.01); *A61K 31/4162* (2013.01); *C07B 2200/13* (2013.01)

(58) Field of Classification Search
CPC .......................... C07D 487/04; A61K 31/4162
See application file for complete search history.

(56) References Cited

U.S. PATENT DOCUMENTS

| | | | |
|---|---|---|---|
| 5,041,442 A | 8/1991 | Romero et al. | |
| 7,326,708 B2 | 2/2008 | Cypes et al. | |
| 8,895,603 B2 * | 11/2014 | Arroyo et al. | 514/407 |
| 2005/0032804 A1 | 2/2005 | Cypes et al. | |
| 2010/0120863 A1 | 5/2010 | Biftu et al. | |
| 2010/0234607 A1 | 9/2010 | Jung et al. | |

FOREIGN PATENT DOCUMENTS

| | | |
|---|---|---|
| CN | 1832949 A | 9/2006 |
| WO | WO02076450 A1 | 10/2002 |
| WO | WO03000180 A2 | 1/2003 |
| WO | WO03000181 A2 | 1/2003 |
| WO | WO03004498 A1 | 1/2003 |
| WO | WO03082817 A2 | 10/2003 |
| WO | WO2004007468 A1 | 1/2004 |
| WO | WO2004032836 A2 | 4/2004 |
| WO | WO2004037169 A2 | 5/2004 |
| WO | WO2004043940 A1 | 5/2004 |
| WO | WO2004050022 A2 | 6/2004 |
| WO | WO2004058266 A1 | 7/2004 |
| WO | WO2004064778 A2 | 8/2004 |
| WO | WO2004069162 A2 | 8/2004 |
| WO | WO2004103276 A2 | 12/2004 |
| WO | WO2004110436 A1 | 12/2004 |
| WO | WO2004112701 A2 | 12/2004 |
| WO | WO2005011581 A2 | 2/2005 |
| WO | WO2005044195 A2 | 5/2005 |
| WO | WO2005108382 A1 | 11/2005 |
| WO | WO2005116029 A1 | 12/2005 |
| WO | WO2006009886 A1 | 1/2006 |
| WO | WO2006023750 A2 | 3/2006 |
| WO | WO2006039325 A2 | 4/2006 |
| WO | WO2006065826 A2 | 6/2006 |
| WO | WO2006078676 A2 | 7/2006 |
| WO | WO2006104997 A2 | 10/2006 |
| WO | WO2006119260 A2 | 11/2006 |
| WO | WO2006127530 A2 | 11/2006 |
| WO | WO2007024993 A2 | 3/2007 |

(Continued)

OTHER PUBLICATIONS

Chawla, G. et al., High-throughput Polymorph Screening of Pharmaceuticals—"Farming for Crystal Mutants", Business Briefing: Future Drug Discovery, 2004, pp. 66-72.

(Continued)

*Primary Examiner* — Samantha Shterengarts
(74) *Attorney, Agent, or Firm* — Janet E. Fair; Anna L. Cocuzzo

(57) ABSTRACT

Novel crystalline forms of (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine are potent inhibitors of dipeptidyl peptidase-IV and are useful for the treatment of non-insulin dependent (Type 2) diabetes mellitus. The invention also relates to pharmaceutical compositions containing these novel forms, processes to prepare these forms and their pharmaceutical compositions as well as uses thereof for the treatment of Type 2 diabetes.

13 Claims, 16 Drawing Sheets

(56) References Cited

FOREIGN PATENT DOCUMENTS

| WO | WO2007035198 A2 | 3/2007 |
| WO | WO2007070434 A2 | 6/2007 |
| WO | WO2007078726 A2 | 7/2007 |
| WO | WO2007087231 A2 | 8/2007 |
| WO | WO2007097931 A2 | 8/2007 |
| WO | WO2007126745 A2 | 11/2007 |
| WO | WO2007136603 A2 | 11/2007 |
| WO | WO2008060488 A1 | 5/2008 |
| WO | WO2009025784 A1 | 2/2009 |
| WO | WO2010056708 A1 | 5/2010 |
| WO | WO2011028455 A1 | 3/2011 |
| WO | WO2011037793 A1 | 3/2011 |
| WO | WO2011146358 A1 | 11/2011 |

OTHER PUBLICATIONS

Florence, A. J., Polymorph screening in pharmaceutical development, European Pharmaceutical Review, 2010, pp. 28-33, No. 4.
Gu, C-H, et al., Grouping solvents by statistical analysis of solvent property parameters: implication to polymorph screening, International Journal of Pharmaceutics, 2004, p. 117-125, vol. 283.

* cited by examiner

US 9,181,262 B2

CRYSTALLINE FORMS OF A DIPEPTIDYL PEPTIDASE-IV INHIBITORS

CROSS REFERENCE TO RELATED APPLICATIONS

This application is continuation of U.S. patent application Ser. No. 14/118, 998, filed 20 Nov. 2013, which is the National Stage of International Application No. PCT/US2012/043922, filed 25 Jun. 2012, which claims the benefit under 35 U.S.C. 119(e) of U.S. Provisional Application No. 61/502,497, filed 29 Jun. 2011.

FIELD OF THE INVENTION

The present invention relates to novel crystalline forms of a dipeptidyl peptidase-IV inhibitor. More particularly, the invention relates to novel crystalline forms of (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine, which is a potent, long acting inhibitor of dipeptidyl peptidase-IV. These novel crystalline forms, are useful for the treatment and prevention of diseases and conditions for which an inhibitor of dipeptidyl peptidase-IV is indicated, in particular Type 2 diabetes, obesity, and high blood pressure. The invention further concerns pharmaceutical compositions comprising the novel crystalline forms of the present invention useful to treat Type 2 diabetes, obesity, and high blood pressure as well as processes for the preparation of such forms and their pharmaceutical compositions.

BACKGROUND OF THE INVENTION

Inhibition of dipeptidyl peptidase-IV (DP-IV), an enzyme that inactivates both glucose-dependent insulinotropic peptide (GIP) and glucagon-like peptide 1 (GLP-1), represents a novel approach to the treatment and prevention of Type 2 diabetes, also known as non-insulin dependent diabetes mellitus (NIDDM). The therapeutic potential of DP-IV inhibitors for the treatment of Type 2 diabetes has been reviewed: C. F. Deacon and J. J. Holst, "Dipeptidyl peptidase IV inhibition as an approach to the treatment and prevention of Type 2 diabetes: a historical perspective," *Biochem. Biophys. Res. Commun.*, 294: 1-4 (2000); K. Augustyns, et al., "Dipeptidyl peptidase IV inhibitors as new therapeutic agents for the treatment of Type 2 diabetes," *Expert. Opin. Ther. Patents*, 13: 499-510 (2003); D. J. Drucker, "Therapeutic potential of dipeptidyl peptidase IV inhibitors for the treatment of Type 2 diabetes," *Expert Opin. Investig. Drugs*, 12: 87-100 (2003); and M. A. Nauck et al., "Incretins and Their Analogues as New Antidiabetic Drugs," *Drug News Perspect.*, 16: 413-422 (2003).

WO 2010/056708 (published 20 May 2010), assigned to Merck & Co., describes a class of aminotetrahydropyrans, which are potent inhibitors of DP-IV and therefore useful for the treatment of Type 2 diabetes. Specifically disclosed in WO 2010/056708 is (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine.

However, the applicants have now discovered novel crystalline forms of (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine (Compound I).

SUMMARY OF THE INVENTION

The present invention is concerned with novel crystalline forms of the dipeptidyl peptidase-IV (DP-IV) inhibitor (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine (Compound I). Certain crystalline forms, have advantages in the preparation of pharmaceutical compositions of (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine, such as ease of processing and crystallisation, handling, stability to stress and dosing. In particular, they exhibit improved physicochemical properties, such as stability to stress, rendering them particularly suitable for the manufacture of various pharmaceutical dosage forms. The invention also concerns pharmaceutical compositions containing the novel forms thereof, as well as methods for using them as DP-IV inhibitors, in particular for the prevention or treatment of Type 2 diabetes, obesity, and high blood pressure. In certain embodiments, described herein are pharmaceutical compositions comprising crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine and a pharmaceutically acceptable carrier.

DETAILED DESCRIPTION OF THE INVENTION

Figure 1:
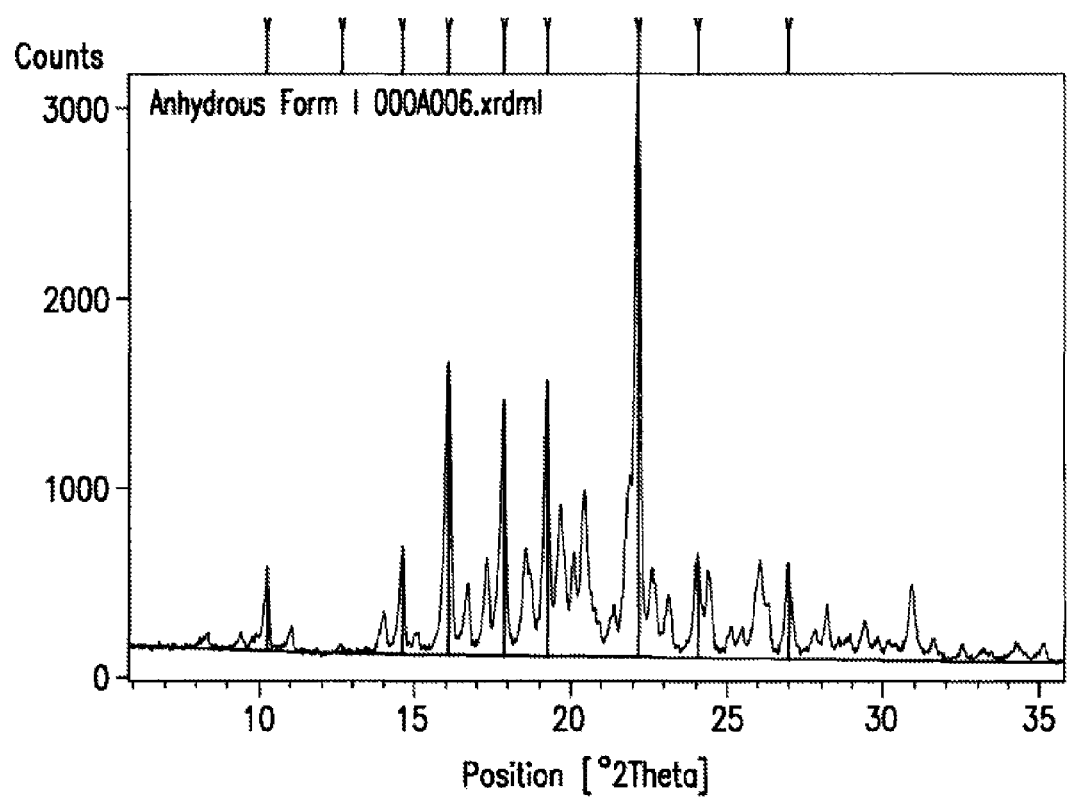
FIG. 1 is a X-ray diffraction pattern of crystalline Form I of Compound I.

This invention relates to crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine of Compound I:

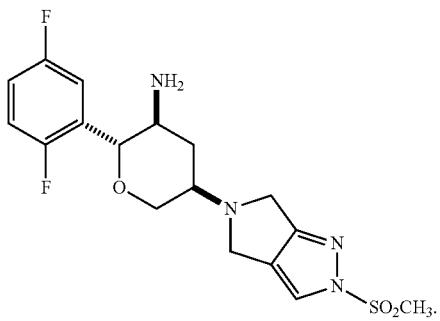

(I)

Unless a specific form designation is given, the term "crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine refers to all crystalline forms of (2R, 3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine described herein. The crystalline forms described herein exist as the anhydrous free base of (2R,3S, 5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine.

One embodiment of the crystalline forms described herein is (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine (Form I). Form I is further described below.

Another embodiment of the crystalline forms described herein is (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine (Form II). Form II is further described below.

Still another embodiment of the crystalline forms described herein is (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine (Form III). Form III is further described below.

Yet another embodiment of the crystalline forms described herein is (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine (Form IV). Form IV is further described below.

A further embodiment of the present invention provides a particular drug substance that comprises at least one of the crystalline forms described herein. By "drug substance" is meant the active pharmaceutical ingredient. The amount of crystalline form in the drug substance can be quantified by the use of physical methods such as X-ray powder diffraction, solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy.

In a class of this embodiment, the crystalline form of the present invention is present in about 5% to about 100% by weight of the drug substance. In a second class of this embodiment, the crystalline form of the present invention is present in about 10% to about 100% by weight of the drug substance. In a third class of this embodiment, the crystalline form of the present invention is present in about 25% to about 100% by weight of the drug substance. In a fourth class of this embodiment, the crystalline form of the present invention is present in about 50% to about 100% by weight of the drug substance. In a fifth class of this embodiment, the crystalline form of the present invention is present in about 75% to about 100% by weight of the drug substance. In a sixth class of this embodiment, substantially all of the drug substance is the crystalline form of the present invention, i.e., the drug substance is substantially phase pure crystalline.

In another class of this embodiment, at least 5% by weight of the drug substance is the crystalline form of the present invention. In a yet another class of this embodiment, at least 10% by weight of the drug substance is the crystalline form of the present invention. In a still another class of this embodiment, at least 15% by weight of the drug substance is the crystalline form of the present invention. In another class of this embodiment, at least 20% by weight of the drug substance is the crystalline form of the present invention. In yet another class of this embodiment, at least 25% by weight of the drug substance is the crystalline form of the present invention. In still another class of this embodiment, at least 30% by weight of the drug substance is the crystalline form of the present invention. In another class of this embodiment, at least 35% by weight of the drug substance is the crystalline form of the present invention. In a yet another class of this embodiment, at least 40% by weight of the drug substance is the crystalline form of the present invention. In a still another class of this embodiment, at least 45% by weight of the drug substance is the crystalline form of the present invention. In another class of this embodiment, at least 50% by weight of the drug substance is the crystalline form of the present invention. In yet another class of this embodiment, at least 55% by weight of the drug substance is the crystalline form of the present invention. In still another class of this embodiment, at least 60% by weight of the drug substance is the crystalline form of the present invention. In another class of this embodiment, at least 65% by weight of the drug substance is the crystalline form of the present invention. In a yet another class of this embodiment, at least 70% by weight of the drug substance is the crystalline form of the present invention. In a still another class of this embodiment, at least 75% by weight of the drug substance is the crystalline form of the present invention. In another class of this embodiment, at least 80% by weight of the drug substance is the crystalline form of the present invention. In yet another class of this embodiment, at least 85% by weight of the drug substance is the crystalline form of the present invention. In still another class of this embodiment, at least 90% by weight of the drug substance is the crystalline form of the present invention. In another class of this embodiment, at least 95% by weight of the drug substance is the crystalline form of the present invention. In a yet another class of this embodiment, at least 100% by weight of the drug substance is the crystalline form of the present invention.

The crystalline forms of the present invention exhibit pharmaceutical advantages over the amorphous free base of Compound I as described in WO 2010/056708 in the preparation of a pharmaceutical drug product containing the pharmacologically active ingredient. In particular, the enhanced chemical and physical stability of the crystalline forms constitute advantageous properties in the preparation of solid pharmaceutical dosage forms containing the pharmacologically active ingredient.

The crystalline forms of the present invention, which exhibit long acting, potent DP-IV inhibitory properties, are particularly useful for the prevention or treatment of Type 2 diabetes, obesity, and high blood pressure.

Another aspect of the present invention provides a method for the prevention or treatment of clinical conditions for which an inhibitor of DP-IV is indicated, which method comprises administering to a patient in need of such prevention or treatment a prophylactically or therapeutically effective amount of a crystalline form of the present invention, or a hydrate thereof. Such clinical conditions include diabetes, in particular Type 2 diabetes, hyperglycemia, insulin resistance, and obesity.

The present invention also provides for the use of a crystalline form of Compound I of the present invention for the prevention or treatment in a mammal of clinical conditions for which an inhibitor of DP-IV is indicated, in particular Type 2 diabetes, hyperglycemia, insulin resistance, and obesity.

The present invention also provides for the use of a crystalline form of Compound I of the present invention for the manufacture of a medicament for the prevention or treatment in a mammal of clinical conditions for which an inhibitor of DP-IV is indicated, in particular Type 2 diabetes, hyperglycemia, insulin resistance, and obesity.

The present invention also provides pharmaceutical compositions comprising a crystalline form described herein, in association with one or more pharmaceutically acceptable carriers or excipients. In one embodiment the pharmaceutical composition comprises a therapeutically effective amount of the active pharmaceutical ingredient in admixture with pharmaceutically acceptable excipients wherein the active pharmaceutical ingredient comprises a detectable amount of a crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine.

In a second embodiment the pharmaceutical composition comprises a therapeutically effective amount of the active pharmaceutical ingredient in an admixture with pharmaceutically acceptable excipients wherein the active pharmaceutical ingredient comprises about 1% to about 100% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a class of this second embodiment, the active pharmaceutical ingredient in such compositions comprises about 5% to about 100% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a second class of this embodiment, the active pharmaceutical ingredient in such compositions comprises about 10% to about 100% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a third class of this embodiment, the active pharmaceutical ingredient in such compositions comprises about 25% to about 100% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a fourth class of this embodiment, the active pharmaceutical ingredient in such compositions comprises about 50% to about 100% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine.

In a third embodiment the pharmaceutical composition comprises a therapeutically effective amount of the active pharmaceutical ingredient in an admixture with pharmaceutically acceptable excipients wherein the active pharmaceutical ingredient comprises at least 1% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a class of this second embodiment, the active pharmaceutical ingredient in such compositions comprises about 5% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a second class of this embodiment, the active pharmaceutical ingredient in such compositions comprises at least 10% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a third class of this embodiment, the active pharmaceutical ingredient in such compositions comprises at least 25% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine. In a fourth class of this embodiment, the active pharmaceutical ingredient in such compositions comprises at least 50% by weight of crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 200 mg of active ingredient. Intravenously, the most preferred doses will range from about 0.1 to about 10 mg/kg/minute during a constant rate infusion. The crystalline forms of the present invention may be administered in a single daily dose, or the total daily dosage may be administered in divided doses of two, three or four times daily. However, (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine is a long acting DPP-IV inhibitor. Advantageously, the crystalline forms of the present invention may be administered in a single weekly dose.

Furthermore, the crystalline forms of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the crystalline forms described herein can form the active pharmaceutical ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug component can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The crystalline forms of Compound I of the present invention have been found to possess a relatively high solubility in water (about 2 mg/ml), rendering them especially amenable to the preparation of formulations, in particular intranasal and intravenous formulations, which require relatively concentrated aqueous solutions of active pharmaceutical ingredient.

In a still further aspect, the present invention provides a method for the treatment and/or prevention of clinical conditions for which a DP-IV inhibitor is indicated, which method comprises administering to a patient in need of such prevention or treatment a prophylactically or therapeutically effective amount of a crystalline form of Compound I as defined above in combination with another agent useful for the treatment of Type 2 diabetes, obesity, and high blood pressure.

Compounds described herein may exist as tautomers such as keto-enol tautomers. The individual tautomers as well as mixtures thereof are encompassed with compounds of structural formula I.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compound I can be made by the following methods:

INTERMEDIATE 1

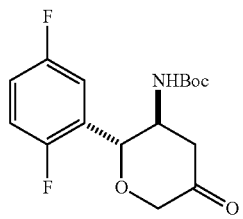

tert-Butyl [(2R,3S)-5-oxo-2-(2,5-difluorophenyl) tetrahydro-2H-pyran-3-yl]carbamate Step A: tert-Butyl (1-[methoxy(methyl)amino]-1-oxopent-4-yn-2-yl)carbamate To an inerted vessel was charged N,N-diphenyl glycine ethyl ester (105.45 kg, 394.5 mol), tetrabutyl ammonium bromide (14 kg, 43.4 mol), and propargyl benzenesulfonate (94.45 kg, 481 mol) followed by MTBE (750 kg). Then cesium carbonate (fine mesh grade, 390 kg, 1197 mol) was added and the reaction stirred at 50-60° C. for 1 day. The batch was then cooled to 0-5° C. and water (422 kg) was slowly added. Next, tert-butyl methyl ether (170 kg) was added and the batch concentrated to 473-578 L. Then, 462 kg HCl solution (43 kg conc. HCl in 420 kg water) was added to reach a pH=1-2 below room temperature. After 7 h of stirring, the pH was 1.5 and the organic layer was separated and discarded.

The aqueous layer was then cooled to 5-10° C. and 28% aqueous NaOH (151 kg) was added slowly until the pH was 13. Then, a solution of Boc$_2$O (136 kg, 624 mol in 243 kg of tert-butyl methyl ether) was added at 5-10° C. The solution was then stirred at room temperature for 4 h (pH=8) and 17% aqueous NaOH (126 kg) was slowly added followed by more Boc$_2$O solution (30.7 kg, 141 mol in 60 kg tert-butyl methyl ether). The solution was then stirred at room temperature for 4 h (pH=9) and 17% aqueous NaOH (98 kg) was slowly added (pH=13) and stirred an additional 12 h (pH=10) followed by more Boc$_2$O (11 kg, 50 mol). After 4 h of stirring at room temperature, the layers were separated (retained aqueous) and the organics extracted with 3% aqueous NaOH (136 kg). The aqueous layers were combined and added to tert-butyl methyl ether (338 kg). Then, aqueous 17% HCl (362 kg) was added until pH=2. The layers were separated and the aqueous extracted with tert-butyl methyl ether (420 kg). The combined organics were washed with 10% brine (139 kg), dried with Na$_2$SO$_4$, filtered, and concentrated to 105-158 L. Constant volume distillation with tert-butyl methyl ether continued until KF=0.4%.

Carbonyldiimidazole (90 kg, 548 mol) was added to this solution and stirred for 2 h at room temperature. Then (MeO)MeNH$_2$Cl (48 kg, 492 mol) was added and the reaction stirred for 6 h. The batch was then cooled to 0-5° C. and water (80 kg) was added. The batch was then seeded with 100 g seed and water (450 kg) was added. The slurry was stirred at 0-5° C. for 3 h and then filtered. The cake was dried under vacuum at 45-60° C. for 2 days to give tert-butyl (1-[methoxy(methyl)amino]-1-oxopent-4-yn-2-yl)carbamate.

Step B: tert-Butyl [1-(2,5-difluorophenyl)-1-oxopent-4-yn-2-yl]carbamate

An inerted vessel was charged dichloromethane (866 kg) and cooled to −20 to −10° C. Then iso-propylmagnesium chloride solution in THF (2M, 326.1 kg, 669 mol) was slowly added followed by 1-bromo-2,5-difluorobenzene (120.1 kg, 622 mol). After 2 h at this temperature, an additional charge of iso-propylmagnesium chloride in THF solution was slowly added (2M, 58.65 kg, 121 mol) and the reaction aged 1 h. Then, a drop-wise addition of a dichloromethane solution of tert-butyl (1-[methoxy(methyl)amino]-1-oxopent-4-yn-2-yl) carbamate (70.8 kg, 276 mol in 292 kg dichloromethane) was conducted over 2 h at −20 to −20° C. The mixture was then warmed to room temperature and stirred for 10 h. The reaction was then slowly reverse quenched into aqueous ammonium chloride (175.6 kg in 1550 kg of water) at 5-10° C. The solution pH was then adjusted to ~7 by adding 68 kg of con. HCl. The layers were then separated and the aqueous extracted with dichloromethane (414 kg). The combined organics were then dried with Na$_2$SO$_4$, filtered, treated with activated carbon (10 kg), filtered, and concentrated to 71-141 L. A constant volume (71-141 L) vacuum distillation solvent switch to n-heptane was then performed to crystallize the product. The slurry was then cooled to 0° C. and stirred 2 h. The slurry was filtered and the cake washed with n-heptane, 2-propanol, and then water. The solids were dried under vacuum at 40-50° C. overnight to give tert-butyl [1-(2,5-difluorophenyl)-1-oxopent-4-yn-2-yl]carbamate.

Step C: tert-Butyl [(1S,2S)-1-(2,5-difluorophenyl)-1-hydroxypent-4-yn-2-yl]carbamate To a stirred vessel under nitrogen sweep was charged tert-butyl [1-(2,5-difluorophenyl)-1-oxopent-4-yn-2-yl]carbamate (35.0 kg, 113 mol), 1,4-diazabicyclo[2.2.2]octane (38.0 kg, 339 mol), and THF (465 kg). After dissolution, chloro{[(1R,2R)-(+2-amino-1,2-diphenylethyl](pentafluorophenyl-sulfonyl)amido}-(p-cymene) ruthenium (II) (410 g, 576 mmol) was added. The vessel was vacuum sparged and back-filled with nitrogen three times. Then, formic acid (26.7 kg, 580 mol) was added and the reaction heated to 45° C. overnight.

The mixture was then concentrated under vacuum to 210-280 L and tert-butyl methyl ether was then added (210 kg). After cooling to 0-10° C., 0.4% aqueous HCl was added (52 kg) until pH=4-6. After agitation and separation of the layers, the aqueous was extracted again with tert-butyl methyl ether (87 kg). The combined organics were then washed with 4% aq. NaHCO$_3$ (291 kg), and then brine (216 kg). The resulting organics were dried over Na$_2$SO$_4$, filtered through a plug of silica, and concentrated to 70-105 L. Then, tert-butyl methyl ether (132 kg) was added, followed by further batch concentration until KF=0.1%. Next, DMF (133 kg) was added and the batch was further concentrated to 70-105 L. The resulting DMF solution was 165.6 kg containing 19.4% tert-butyl [(1S,2S)-1-(2,5-difluorophenyl)-1-hydroxypent-4-yn-2-yl]carbamate (8.1/1 diastereomeric ratio and 97.9% ee).

Step D: tert-Butyl [(1S,2R)-1-(2,5-difluorophenyl)-1-hydroxypent-4-yn-2-yl]carbamate This compound was made by following the same method described in Intermediate 1, Step C.

Step E: tert-Butyl [(1R,2R)-1-(2,5-difluorophenyl)-1-hydroxypent-4-yn-2-yl]carbamate This compound was made by following the same method described in Intermediate 1, Step D.

Step F: tert-Butyl [(1R,2S)-1-(2,5-difluorophenyl)-1-hydroxypent-4-yn-2-yl]carbamate This compound was made by following the same method described in Intermediate 1, Step E.

Step G: tert-Butyl [(2R,3S)-2-(2,5-difluorophenyl)-3,4-dihydro-2H-pyran-3-yl]carbamate To a 165.6 kg solution of tert-butyl [(1S,2S)-1-(2,5-difluorophenyl)-1-hydroxypent-4-yn-2-yl]carbamate (19.4 w/w % in DMF, 103 mol) was added DMF (70 kg), 1-hydroxypyrrolidine-2,5-dione (5.95 kg, 51 mol), tetrabutylammonium hexafluorophosphate (5.20 kg, 13 mol), and NaHCO$_3$ (4.50 kg, 54 mol). The resulting reaction mixture was vacuum sparged with a nitrogen back-fill three times and then stirred for 30-40 min. Then, chloro(cyclopentadienyl)bis(triphenylphosphine) ruthenium (II) (823 g, 1.13 mol) and triphenylphosphine (892 g, 3.40 mol) was added and the reaction was vacuum purged with nitrogen back-filling three times. The reaction was then heated to 75-85° C. overnight. To complete the reaction, additional chloro(cyclopentadienyl) bis(triphenylphosphine) ruthenium (II) (826 g, 1.14 mol) and triphenylphosphine (892 g, 3.40 mol) was added and the reaction heated at 75-85° C. an additional 12-16 h.

After cooling to room temperature, water (250 kg) and tert-butyl methyl ether (210 kg) was added. After agitation, the layers were separated and the resulting aqueous layer was extracted with tert-butyl methyl ether (2×150 kg). The combined organics were washed with brine (4×220 kg). The organics were then dried with Na$_2$SO$_4$, filtered, and concentrated. The crude was passed through a plug of silica with tert-butyl methyl ether and n-heptane. The resulting solution was then solvent switched by vacuum distillation and feeding n-heptane to a slurry of 64-128 L in n-heptane. This slurry was heated to dissolve at 90-110° C. This was then cooled over 2-3 h to 0-10° C. The slurry was then filtered and the resulting wet cake dried at 40-50° C. and vacuum to give tert-butyl [(2R,3S)-2-(2,5-difluorophenyl)-3,4-dihydro-2H-pyran-3-yl]carbamate.

Step H: tert-Butyl [(2R,3R)-2-(2,5-difluorophenyl)-3,4-dihydro-2H-pyran-3-yl]carbamate This compound was made by following the same method described in Intermediate 1, Step G.

Step I: tert-Butyl [(2S,3S)-2-(2,5-difluorophenyl)-3,4-dihydro-2H-pyran-3-yl]carbamate This compound was made by following the same method described in Intermediate 1, Step H.

Step J: tert-Butyl [(2S,3R)-2-(2,5-difluorophenyl)-3,4-dihydro-2H-pyran-3-yl]carbamate This compound was made by following the same method described in Intermediate 1, Step I.

Step K: tert-Butyl [(2R,3S)-2-(2,5-difluorophenyl)-5-hydroxytetrahydro-2H-pyran-3-yl]carbamate To 64.0 kg (206 mol) of tert-butyl [(2R,3S)-2-(2,5-difluorophenyl)-3,4-dihydro-2H-pyran-3-yl]carbamate in a stirred vessel was added tert-butyl methyl ether (500 kg). After dissolving, the solution was cooled to 0-5° C. and 10M borane-dimethyl sulfide complex solution was added (39 kg, 515 mol). After 1-3 h of stirring at this temperature, water (35 kg) was slowly added and the solution stirred for 2 h at 0-10° C. Then, 3% aqueous NaHCO3 (900 kg) and 1% aqueous NaOH (582 kg) was added. Next, NaBO$_3$.4H$_2$O (115.6 kg, 751 mol) was added portion-wise over 1 h at 0-10° C. After stirring the reaction overnight at room temperature, additional NaBO$_3$.4H$_2$O (25.7 kg, 167 mol) was added portion-wise over 1 h at 0-10° C. The reaction was then stirred an additional 6 h at room temperature.

The reaction was then extracted with ethyl acetate (230 kg) and the resulting organics washed with 3% aqueous NaHCO$_3$ (500 kg), followed by brine (376 kg). The combined aqueous layers were further extracted with ethyl acetate (2×325 kg). The organics were then treated with activated carbon (14.4 kg) for 2 h at 50-60° C. After filtration, the organics were then concentrated and solvent switched to n-heptane to form a crystalline slurry. This slurry was then filtered and the cake was washed with n-heptane. This wet cake was then dissolved in ethyl acetate (99 kg) at 50-60° C. n-Heptane (251 kg) was then added and the batch cooled to 0° C. The resulting slurry was then filtered and the cake washed with n-heptane. The solids were then dried at 40-50° C. under vacuum to give tert-butyl [(2R,3S)-2-(2,5-difluorophenyl)-5-hydroxytetrahydro-2H-pyran-3-yl]carbamate.

Step L: tert-Butyl [(2R,3R)-2-(2,5-difluorophenyl)-5-hydroxytetrahydro-2H-pyran-3-yl]carbamate This compound was made by following the same method described in Intermediate 1, Step K.

Step M: tert-Butyl [(2S,3R)-2-(2,5-difluorophenyl)-5-hydroxytetrahydro-2H-pyran-3-yl]carbamate This compound was made by following the same method described in Intermediate 1, Step L.

Step N: tert-Butyl [(2S,3S)-2-(2,5-difluorophenyl)-5-hydroxytetrahydro-2H-pyran-3-yl]carbamate This compound was made by following the same method described in Intermediate 1, Step M.

Step O: tert-Butyl [(2R,3S)-2-(2,5-difluorophenyl)-5-oxotetrahydro-2H-pyran-3-yl]carbamate To 46.8 kg (142 mol) of tert-butyl [(2R,3S)-2-(2,5-difluorophenyl)-5-hydroxytetrahydro-2H-pyran-3-yl]carbamate in a stirred vessel was added acetonitrile (150 kg), acetic acid (50 kg), and water (25 kg). After dissolving at room temperature, the solution was cooled to 0° C. and RuCl$_3$.3H$_2$O (250 g, 956 mmol) in water (50 kg) was added under nitrogen. Then, NaBrO$_3$ (11.7 kg, 77.5 mol) was added in six portions every 1.5 h under nitrogen. After stirring at 0° C. for 6 h, 2-propanol (31 kg) was added over 30 min. at 0° C. Then, water (720 kg) was added at this temperature over 5 h. The resulting slurry was stirred overnight, filtered, and cake washed with water. The solids were then dried under vacuum at 40-60° C. to give tert-butyl [(2R,3S)-2-(2,5-difluorophenyl)-5-oxotetrahydro-2H-pyran-3-yl]carbamate.

INTERMEDIATE 2

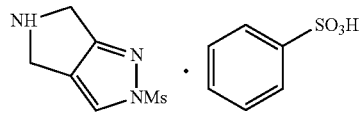

2-(methylsulfonyl)-2,4,5,6-tetrahydropyrrolo[3,4-c]pyrazol-5-ium benzenesulfonate Step A: tert-Butyl (3Z)-3-[(dimethylamino)methylene]-4-oxopyrrolidine-1-carboxylate A solution of tert-butyl 3-oxopyrrolidine-1-carboxylate (53.4 kg, 288 mol) in THF (133 kg) was treated with DMF-DMA (103 kg, 864 mol) in THF (472 kg) and heated at 65-70° C. under nitrogen for 20 h. The solution was cooled, evaporated under reduced pressure and solvent switched under distillation to cyclohexane. The resulting slurry was then filtered, cake washed with cyclohexane, and then water. The solids were then dried under vacuum at 35-40° C. to give tert-butyl (3Z)-3-[(dimethylamino)methylene]-4-oxopyrrolidine-1-carboxylate.

Step B: tert-Butyl 6a-hydroxy-3a,4,6,6a-tetrahydropyrro[3,4-c]pyrazole-5(1H)-carboxylate To a solution of tert-butyl (3Z)-3-[(dimethylamino)methylene]-4-oxopyrrolidine-1-carboxylate (58.2 kg, 242 mol) in toluene (251 kg) at 35-45° C. was added hydrazine hydrate (14.6 kg, 290 mol) via drop-wise addition over 2 h. The mixture was then stirred for 10 h at this temperature. The batch was then cooled to 0-10° C. and the slurry stirred for 6 h. This slurry was then filtered and the cake washed with n-heptane. The solids were then dried under vacuum overnight at 35-50° C. to give tert-butyl 6a-hydroxy-3a,4,6,6a-tetrahydropyrrol[3,4-c]pyrazole-5(1H)-carboxylate.

Step C: tert-Butyl 4,6-dihydropyrrolo[3,4-c]pyrazole-5(1H)-carboxylate

To a solution of tert-butyl 6a-hydroxy-3a,4,6,6a-tetrahydropyrrol[3,4-c]pyrazole-5(1H)-carboxylate (47.0 kg, 207 mol) in dichloromethane (669 kg) at 0° C. was added a methanol solution of toluene-4-sulfonic acid monohydrate (3.7 kg, 20 mol in 38 kg MeOH) drop-wise over 2 h. The reaction was then aged for 4 h at this temperature. Then, 5% aqueous NaHCO$_3$ (91 kg) was added and stirred at room temperature for 30 min. The layers were then separated and the aqueous extracted with dichloromethane (312 kg). The combined organics were washed with 5% brine (190 kg then 483 kg), treated with activated carbon (2.7 kg) and filtered. The resulting organics were dried with Na$_2$SO$_4$, filtered, and concentrated to 71-118 L. n-Heptane was then added (238 kg) and the batch further concentrated to 188-235 L. The slurry was cooled to 10-20° C., filtered, and the cake washed with n-heptane. The solids were dried under vacuum at 40-50° C. overnight to give tert-butyl 4,6-dihydropyrrolo[3,4-c]pyrazole-5(1H)-carboxylate.

Step D: tert-Butyl 2-(methylsulfonyl)-2,6-dihydropyrrolo[3,4-c]pyrazole-5(4H)-carboxylate A solution of tert-butyl 4,6-dihydropyrrolo[3,4-c]pyrazole-5(1H)-carboxylate (30.0 kg, 143 mol) in 2-methyltetrahydrofuran (384 mg) was vacuum purged with nitrogen back-fill three times. The, triethylamine (25.0 kg, 247 mol) was added and the batch cooled to −10-5° C. Then, methanesulfonyl chloride (21.4 kg, 187 mol) was slowly added over 2 h. After stirring for 1 h at room temperature, water (150 kg) was added drop-wise at 5-15° C. This was followed by addition of 1N HCl solution until the pH was 7. The resulting layers were separated and the aqueous extracted with 2-methyltetrahydrofuran (106 kg). The combined organics were washed with saturated brine (2×150 kg), dried with Na$_2$SO$_4$, filtered, and concentrated to 60-90 L.

The resulting crude was dissolved in 2-methyltetrahydrofuran (381 kg) and charged with a solution of potassium tert-butoxide in THF (805 g in 6.6 kg THF). After stirring 1 h at room temperature under nitrogen, more potassium tert-butoxide in THF (329 g in 3.0 kg THF) was added and stirred for 1 h. Analytical analysis indicates that tert-butyl 2-(methylsulfonyl)-2,6-dihydropyrrolo[3,4-c]pyrazole-5(4H)-carboxylate is the major regioisomer, so saturated brine (154 kg) was then added. After brief agitation, the layers are separated and the oragnics are washed with saturated brine (2×155 kg). The combined aqueous waste layers were then extracted with 2-methyltetrahydrofuran (103 kg). The combined organics were treated with activated carbon (8.75 kg), filtered, and dried with Na$_2$SO$_4$. This was then filtered and concentrated to 60-90 L. This slurry was then heated to dissolve solids at 40-50° C. and n-heptane was added (34 kg). After cooling to room temperature for 2-4 h, n-heptane (156 kg) was added and the slurry was then aged for 2-4 h at 0-5° C. The slurry was filtered and the cake washed with n-heptane. The solids were dried under vacuum at 45-55° C. to give tert-butyl 2-(methylsulfonyl)-2,6-dihydropyrrolo[3,4-c]pyrazole-5 (4H)-carboxylate.

Step E: tert-Butyl 1-(methylsulfonyl)-4,6-dihydropyrrolo[3,4-c]pyrazole-5(1H)-carboxylate This compound was made by following the same method described in Intermediate 1, Step D.

Step F: 2-(methylsulfonyl)-2,4,5,6-tetrahydropyrrolo [3,4-c]pyrazol-5-ium benzenesulfonate To a solution of tert-butyl 2-(methylsulfonyl)-2,6-dihydropyrrolo[3,4-c]pyrazole-5(4H)-carboxylate (32.1 kg, 111 mol) in iso-propylacetate (289 kg) was added benzenesulfonic acid (35.35 kg, 223 mol). The reaction was stirred for 3 days at room temperature and then cooled to 0-10° C. and stirred an additional 1 h. The resulting slurry was filtered and the cake washed with iso-propylacetate. The solids were dried overnight under vacuum at room temperature to give 2-(methylsulfonyl)-2,4,5,6-tetrahydropyrrolo[3,4-c]pyrazol-5-ium benzenesulfonate.

(2R,3S,5R)-2-(2,5-Difluorophenyl)-5-[2-(methylsulfonyl)-2,6-dihydropyrrolo[3,4-c]pyrazol-5(4H)-yl] tetrahydro-2H-pyran-3-amine

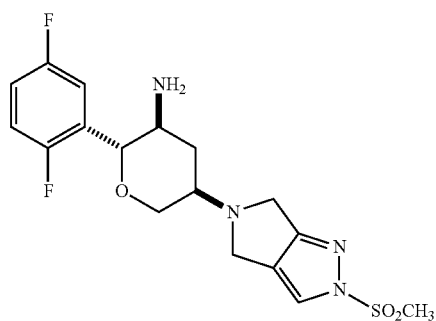

(I)

Step A: tert-Butyl {(2R,3S,5R)-2-(2,5-difluorophenyl)-5-[2-(methylsulfonyl)-2,6-dihydropyrrolol[3,4-c]pyrazol-5(4H)-yl]tetrahydro-2H-pyran-3-yl}carbamate A vessel was charged with N,N-dimethylacetamide (520.6 kg), 2-(methylsulfonyl)-2,4,5,6-tetrahydropyrrolo[3,4-c] pyrazol-5-ium benzenesulfonate (intermediate 2, 30.0 kg, 86.8 mol), and tert-butyl [(2R,3S)-2-(2,5-difluorophenyl)-5-oxotetrahydro-2H-pyran-3-yl]carbamate (intermediate 1, 31.2 kg, 95.3 mol). After dissolving at room temperature, the solution was cooled to 0-10° C. and sodium triacetoxyborohydride (24 kg, 113 mol) was added in four equal portions every 40 min. The reaction was then allowed to warm to room temperature and stirred an additional 5 h. The solution was then cooled to 5-15° C. and water (672 kg) was added over 1-2 h. The resulting slurry was filtered and the cake washed sequentially with N,N-dimethylacetamide, twice with water, and then n-heptane. The solids were dried under vacuum at 40-60° C. to give tert-butyl {(2R,3S,5R)-2-(2,5-difluorophenyl)-5-[2-(methylsulfonyl)-2,6-dihydropyrrolo[3,4-c]pyrazol-5(4H)-yl]tetrahydro-2H-pyran-3-yl}carbamate.

Step B: (2R,3S,5R)-2-(2,5-Difluorophenyl)-5-[2-(methylsulfonyl)-2,6-dihydropyrrolo[3,4-c]pyrazol-5 (4H)-yl]tetrahydro-2H-pyran-3-amine Benzenesulfonic acid (32.95 kg, 271 mol) was dissolved in dichloromethane (1020 kg) under nitrogen. Then, 880 g of water was added such that the solution KF was 0.2%. Next, tert-butyl {(2R,3S,5R)-2-(2,5-difluorophenyl)-5-[2-(methylsulfonyl)-2,6-dihydropyrrolo[3,4-c]pyrazol-5(4H)-yl]tetrahydro-2H-pyran-3-yl}carbamate (38.4 kg, 100 mol) was added in three equal portions over 30 min. The reaction was then aged overnight at room temperature. Next, water (733 kg) was added over 1 h and the reaction stirred rapidly for 1 h. The layers were then separated, discarding the resulting organics layer. To the aqueous layer was charged dichloromethane (510 kg) followed by triethylamine (22.4 kg, 592 mol). After agitation, the layers were separated and the aqueous extracted with dichloromethane (510 kg). The combined organics were washed with 7% aqueous $NaHCO_3$ (2×410 kg) and 5% brine (386 kg). The organics were then dried with $Na_2SO_4$, filtered, and treated with activated carbon (6.2 kg of C-941). The carbon was filtered off and the filtrate was concentrated under vacuum to 154-193 L. This solution was then warmed to 30-35° C. to dissolve solids (additional dichloromethane may be added to dissolve solids). Next, iso-propylacetate (338 kg) was added and the solution stirred at room temperature for 1.5 h. Then, n-heptane (159 kg) was charged to the vessel drop-wise and stirred for 3 h. The slurry was then filtered and the cake washed with n-heptane. This wet cake was then recrystallized again by dissolving it into dichloromethane and adding iso-propylacetate and n-heptane as before, filtering, and washing with n-heptane. The solids were dried under vacuum at 40-50° C. overnight to give crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine was washed with cold 2:1EtOAc/hexanes to give the title compound as an off-white solid. $^1$H NMR (500 MHz, CD3OD): 1.71 (q, 1H, J=12 Hz), 2.56-2.61 (m, 1H), 3.11-3.18 (m, 1H), 3.36-3.40 (m, 1H), 3.48 (t, 1H, J=12 Hz), 3.88-3.94 (m, 4H), 4.30-4.35 (m, 1H), 4.53 (d, 1H, J=12 Hz), 7.14-7.23 (m, 2H), 7.26-7.30 (m, 1H), 7.88 (s, 1H). LC-MS: 399.04 [M+1].

Form I

Form I was produced by direct crystallization of the amorphous free base of Compound I in ethyl acetate. The characterization results for XRPD, ssNMR, DSC, TGA and IR are shown below.

Form II

Crystalline Form II was produced by re-crystallization of Form I in isopropyl acetate and heptane 1:1 at room temperature. Form II was characterized using XRPD, ssNMR, DSC, TGA and IR. Conversion of Form II into Form I is slow but observed in all turnover experiments with 50-50 seed including DCM-Heptane 25° C. over two days, IPAc 25° C. 17 hr, IPAc 60° C. for one day, $H_2O$ 60° C. over two weeks, three days, NMP-water 1-1 35° C. over three days. The relationship between Form I and Form II is enantiotropic having Form I as the most stable phase above 13° C.

Form III

Form III was produced by dissolving Form I in MeOH and evaporating the solvent, followed by heating to 140° C. and isothermal for 10 min. This phase is metastable to Form I and II and its characterization was limited to the amount of sample available. Form III was analyzed by XRPD and DSC.

Form IV

Form IV was produced by dissolving Form I in 1:1 THF-water and evaporating the solvent. Anhydrous Form IV is metastable to Form I and II and therefore the characterization was limited to the amount of sample available. Form IV was analyzed using XRPD, DSC and TGA.

X-Ray Powder Diffraction

X-ray powder diffraction studies are widely used to characterize molecular structures, crystalinity, and polymorphism. The X-ray powder diffraction patterns for the solid phases for crystalline forms of Compound I were generated on a Philips Analytical X'Pert PRO X-ray Diffraction System with PW3040/60 console. A PW3373/00 ceramic Cu LEF X-ray tube K-Alpha radiation was used as the source. The diffraction peak positions were referenced by silicon (internal standard) which has a 2 theta value of 28.443 degree. The experiments were analyzed at ambient condition.

The crystalline forms described herein have a phase purity of at least about 5% of the form with the above X-ray powder diffraction and DSC physical characteristics. In one embodiment the phase purity is at least about 10% of the form with the above solid-state physical characteristics. In a second embodiment the phase purity is at least about 25% of the form with the above solid-state physical characteristics. In a third embodiment the phase purity is at least about 50% of the form with the above solid-state physical characteristics. In a fourth embodiment the phase purity is at least about 75% of the form with the above solid-state physical characteristics. In a fifth embodiment the phase purity is at least about 90% of the form with the above solid-state physical characteristics. In a sixth embodiment the crystalline forms of the present invention are the substantially phase pure forms with the above solid-state physical characteristics. By the term "phase purity" is meant the solid state purity of the particular form with regard to a particular crystalline form as determined by the solid-state physical methods described in the present application.

FIG. 1 is the X-ray powder diffraction (XRPD) pattern for Form I of Compound I with selected d-spacings listed in Table 1.

TABLE 1

XRPD: Form I of Compound I

| 2θ(2 theta)(degrees) | d-spacing (Å) |
| --- | --- |
| 10.3 | 8.63 |
| 12.7 | 6.99 |
| 14.6 | 6.07 |
| 16.1 | 5.51 |
| 17.8 | 4.97 |
| 19.2 | 4.61 |
| 22.2 | 4.01 |
| 24.1 | 3.70 |
| 26.9 | 3.31 |

Crystalline (2R,3S,5R)-2-(2,5-Difluorophenyl)-5-[2-(methylsulfonyl)-2,6-dihydropyrrolo[3,4-c]pyrazol-5(4H)-yl] tetrahydro-2H-pyran-3-amine (Form I) is characterized by having at least four peaks in its powder X-ray diffraction pattern selected from the group consisting of 10.3±0.1 2θ, 12.7±0.1 2θ, 14.6±0.1 2θ, 16.1±0.1 2θ, 17.8±0.1 2θ, 19.2±0.1 2θ, 22.2±0.1 2θ, 24.1±0.1 2θ and 26.9±0.1 2θ. The crystalline Form 1 can be characterized by the following four peaks in its powder X-ray diffraction pattern 17.8±0.1 2θ, 19.2±0.1 2θ, 22.2±0.1 2θ and 24.1±0.1 2θ. The crystalline Form 1 can be characterized by the following four peaks in its powder X-ray diffraction pattern of FIG. 3.

Figure 6:
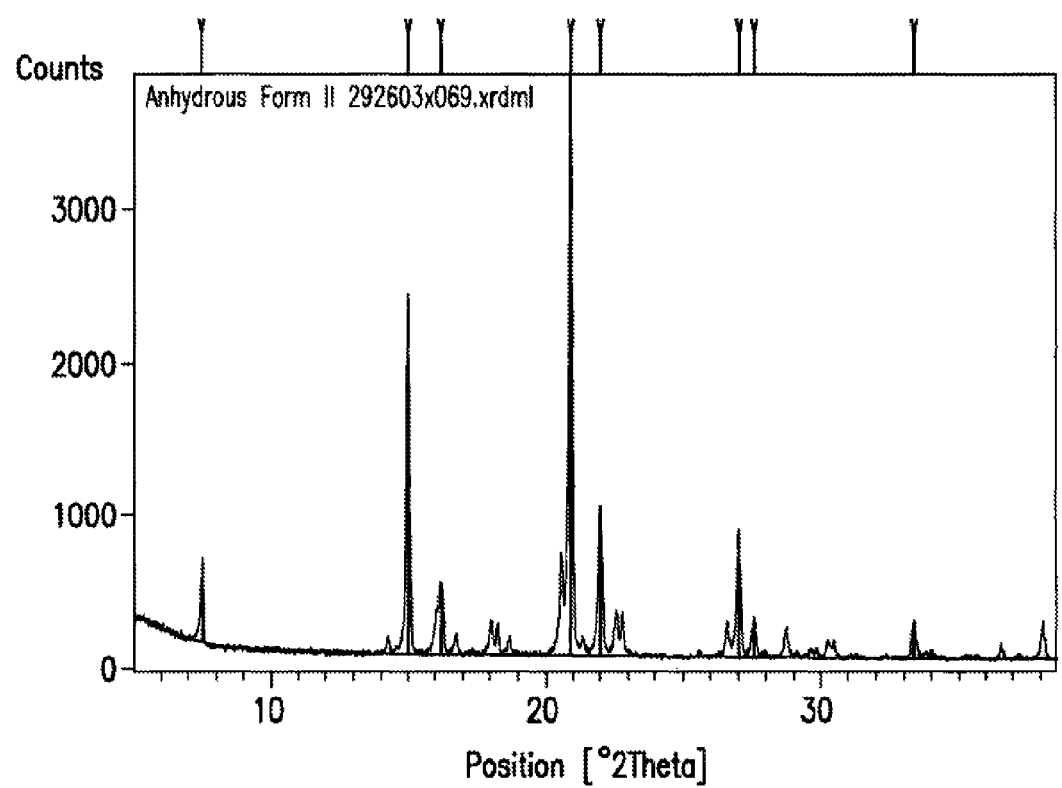
FIG. 6 is a X-ray diffraction pattern of crystalline Form II of Compound I.

FIG. 6 is the X-ray powder diffraction (XRPD) pattern for Form II of Compound I with selected d-spacings listed in Table 2.

TABLE 2

X-ray powder diffraction: Form II of Compound I

| 2θ(2 theta)(degrees) | d-spacing (Å) |
| --- | --- |
| 7.5 | 11.81 |
| 15.0 | 5.91 |
| 16.2 | 5.49 |
| 20.9 | 4.25 |
| 22.0 | 4.04 |
| 27.0 | 3.30 |
| 27.6 | 3.24 |
| 33.3 | 2.69 |

Crystalline (2R,3S,5R)-2-(2,5-Difluorophenyl)-5-[2-(methylsulfonyl)-2,6-dihydropyrrolo[3,4-c]pyrazol-5(4H)-yl] tetrahydro-2H-pyran-3-amine (Form II) can be characterized by having at least four peaks in its powder X-ray diffraction pattern selected from the group consisting of 7.5±0.1 2θ, 15.0±0.1 2θ, 16.2±0.1 2θ, 20.9±0.1 2θ, 22.0±0.1 2θ, 27.0±0.1 2θ, 27.6±0.1 2θ, 33.3±0.1 2θ. The crystalline Form II can be characterized by the following four peaks in its powder X-ray diffraction pattern 20.9±0.1 2θ, 22.0±0.1 2θ, 27.0±0.1 2θ and 27.6±0.1 2θ. Crystalline Form II of can be characterized by the X-ray powder diffraction pattern of FIG. 6.

Figure 11:
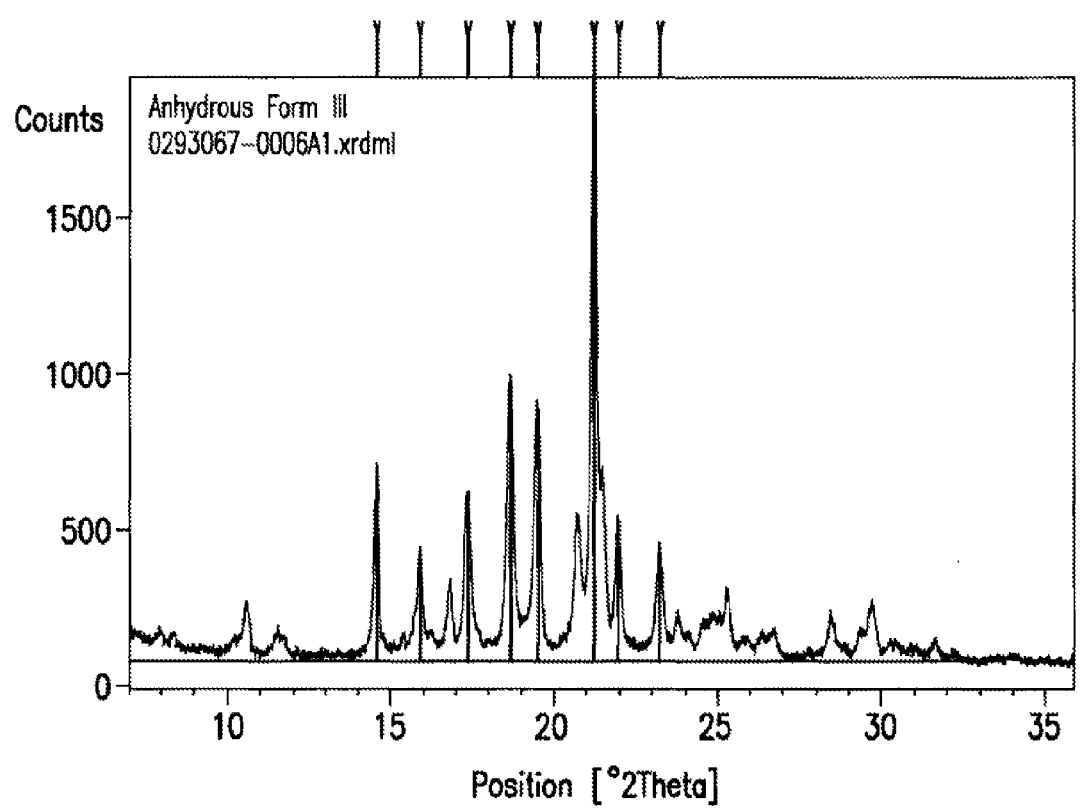
FIG. 11 is a X-ray diffraction pattern of crystalline Form III of Compound I.

FIG. 11 is the X-ray powder diffraction (XRPD) pattern for Form III of Compound I with selected d-spacings listed in Table 3.

TABLE 3

X-ray powder diffraction: Form III of Compound I

| 2θ(2 theta)(degrees) | d-spacing (Å) |
| --- | --- |
| 14.5 | 6.09 |
| 15.9 | 5.58 |
| 17.3 | 5.11 |
| 18.7 | 4.76 |
| 19.5 | 4.56 |
| 21.2 | 4.19 |
| 22.0 | 4.05 |
| 23.2 | 3.83 |

Crystalline (2R,3S,5R)-2-(2,5-Difluorophenyl)-5-[2-(methylsulfonyl)-2,6-dihydropyrrolo[3,4-c]pyrazol-5(4H)-yl] tetrahydro-2H-pyran-3-amine (Form III) can be characterized by having at least four peaks in its powder X-ray diffraction pattern selected from the group consisting of 14.5 +0.1 2θ, 15.9 +0.1 2θ, 17.3 +0.1 2θ, 18.7 +0.1 2θ, 19.5 +0.1 2θ, 21.2 +0.1 2θ, 22.0 +0.1 2θ and 23.2 +0.1 2θ. Crystalline Form III can be characterized by the following four peaks in its powder X-ray diffraction pattern 19.5 +0.1 2θ, 21.2 +0.1

2θ, 22.0 +0.1 2θ and 23.2 +0.1 2θ. Crystalline Form III can be characterized by the X-ray powder diffraction pattern of FIG. 11.

Figure 14:
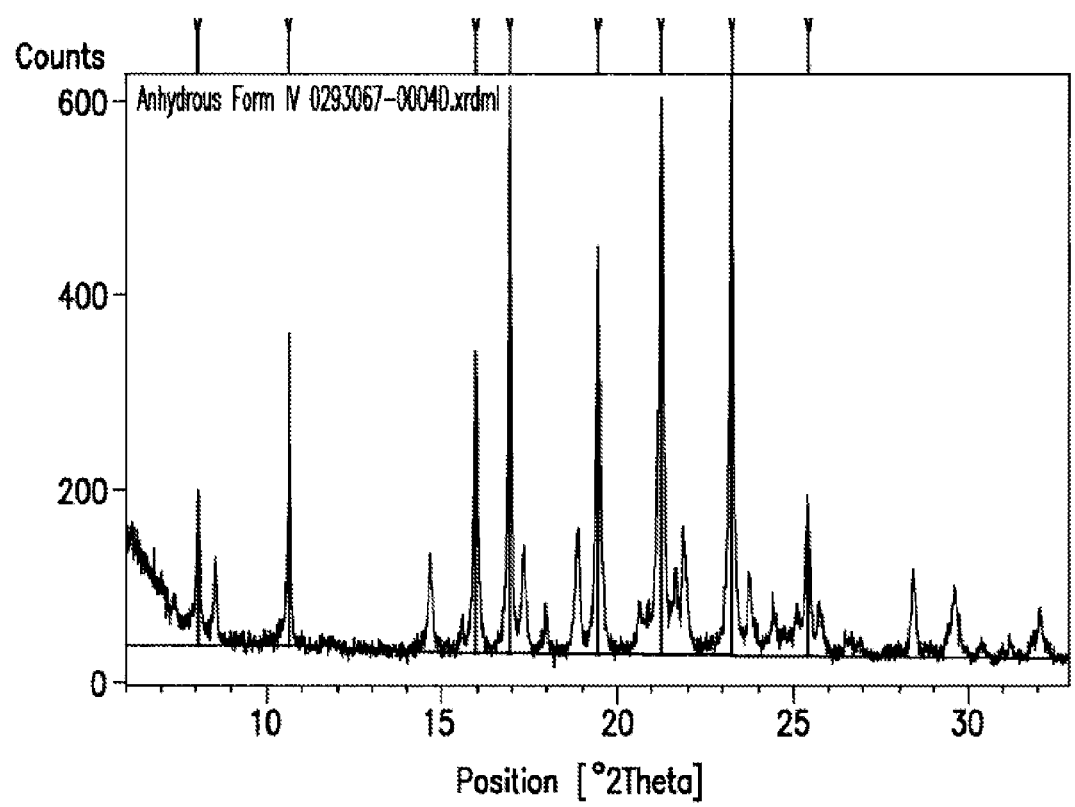
FIG. 14 is a X-ray diffraction pattern of crystalline Form IV of Compound I.

FIG. 14 is the X-ray powder diffraction (XRPD) pattern for Form IV of Compound I with selected d-spacings listed in Table 4.

TABLE 4

X-ray powder diffraction: anhydrous Form IV of Compound I

| 2θ(2 theta)(degrees) | d-spacing (Å) |
|---|---|
| 8.1 | 10.98 |
| 10.6 | 8.33 |
| 16.0 | 5.55 |
| 16.9 | 5.24 |
| 19.5 | 4.56 |
| 21.3 | 4.18 |
| 23.3 | 3.82 |

Crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine (Form IV) can be characterized by having at least four peaks in its powder X-ray diffraction pattern selected from the group consisting of 8.1±0.1 2θ, 10.6±0.1 2θ, 16.0±0.1 2θ, 16.9±0.1 2θ, 19.5±0.1 2θ, 21.3±0.1 2θ, 23.3±0.1 2θ and 25.4±0.1 2θ. Crystalline Form IV can be characterized by the following four peaks in its powder X-ray diffraction pattern 16.9±0.1 2θ, 19.5±0.1 2θ, 21.3±0.1 2θ and 23.3±0.1 2θ. Crystalline Form IV can be characterized by the X-ray powder diffraction pattern of FIG. 14.

ssNMR Spectra

Solid-state carbon-13 nuclear magnetic resonance spectrum was recorded on a Bruker AV400 NMR spectrometer using a Bruker 4 mm H/F/X BB double resonance CPMAS probe. The spectrum were collected utilizing proton/carbon-13 variable-amplitude cross-polarization (VACP) at 10 kHz, with a contact time of 3 ms. Other experimental parameters used for data acquisition were a proton 90-degree pulse of 100 kHz, SPINAL64 decoupling at 100 kHz, a pulse delay of 5 s, and signal averaging for 1024 scans. The magic-angle spinning (MAS) rate was set to 10 kHz. A Lorentzian line broadening of 10 Hz was applied to the spectrum before Fourier Transformation. Chemical shifts are reported on the TMS scale using the carbonyl carbon of glycine (176.70 ppm.) as a secondary reference.

Figure 4:
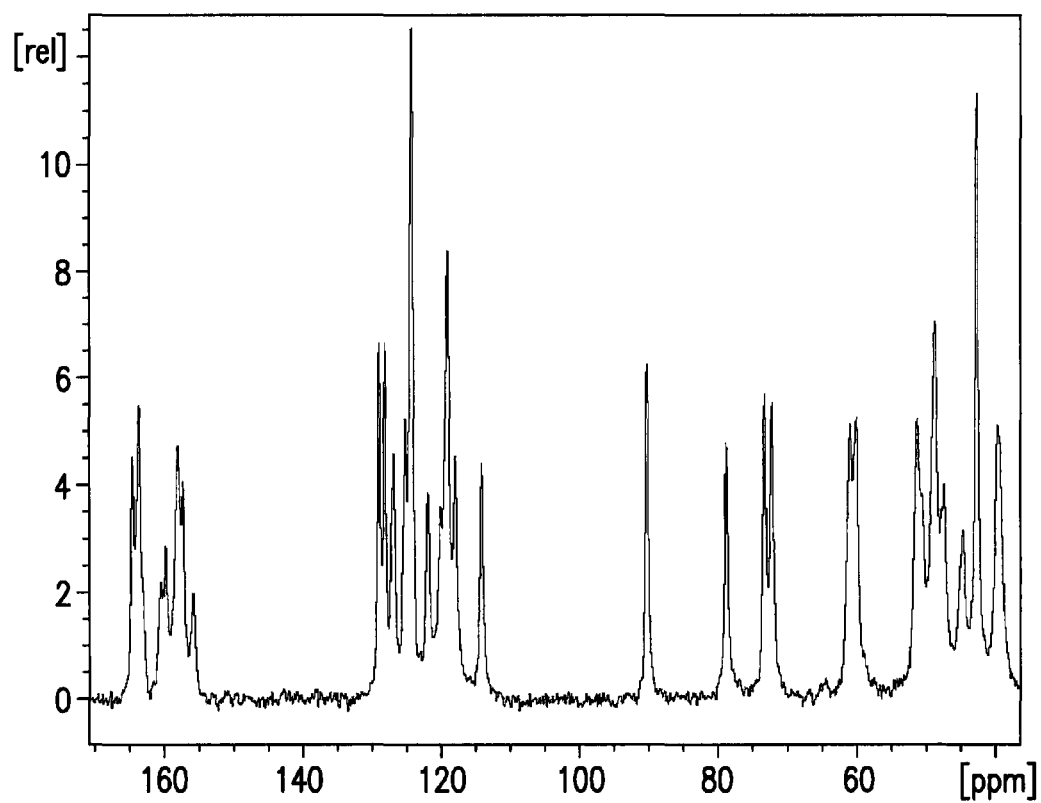
FIG. 4 is a solid state NMR spectra of crystalline Form I of Compound I.

Crystalline Form I can further characterized by the nuclear magnetic resonance (NMR) spectra of FIG. 4. FIG. 4 is the ssNMR spectra for Form I of Compound I with selected peaks listed in Table 5.

TABLE 5

Selected ssNMR peaks for Form I of Compound I

| Peak (ppm) | Relative Intensity |
|---|---|
| 124.3 | 100 |
| 42.6 | 91 |
| 119.0 | 67 |
| 48.6 | 56 |
| 128.9 | 53 |
| 90.1 | 50 |
| 73.2 | 46 |
| 163.6 | 44 |
| 59.9 | 42 |
| 157.9 | 38 |

Figure 9:
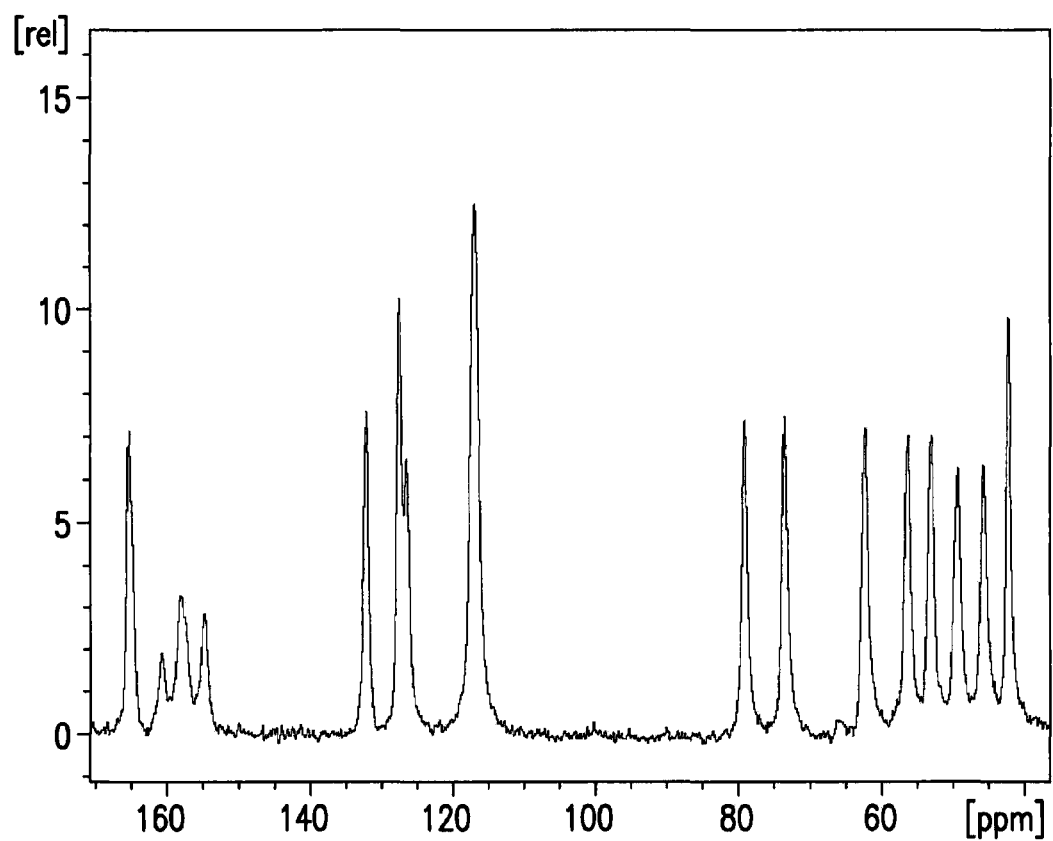
FIG. 9 is a solid state NMR spectra of crystalline Form II of Compound I.

Crystalline Form II can be further characterized by the nuclear magnetic resonance (NMR) spectra of FIG. 9. FIG. 9 is the ssNMR spectra for Form II of Compound I with selected peaks listed in Table 6.

TABLE 6

Selected ssNMR peaks for Form II of Compound I

| Peak (ppm) | Relative Intensity |
|---|---|
| 116.9 | 100 |
| 127.5 | 82 |
| 42.2 | 78 |
| 132.1 | 61 |
| 73.5 | 60 |
| 79.0 | 59 |
| 62.3 | 57 |
| 165.3 | 57 |
| 53.0 | 56 |
| 56.3 | 56 |

IR Spectra

The Infrared spectrum was obtained using Attenuated Total Reflectance (ATR). The sample was placed directly onto the ATR-FTIR sampling device and the infrared spectrum was recorded using a Nicolet Nexus 670 FTIR spectrometer.

Figure 5:
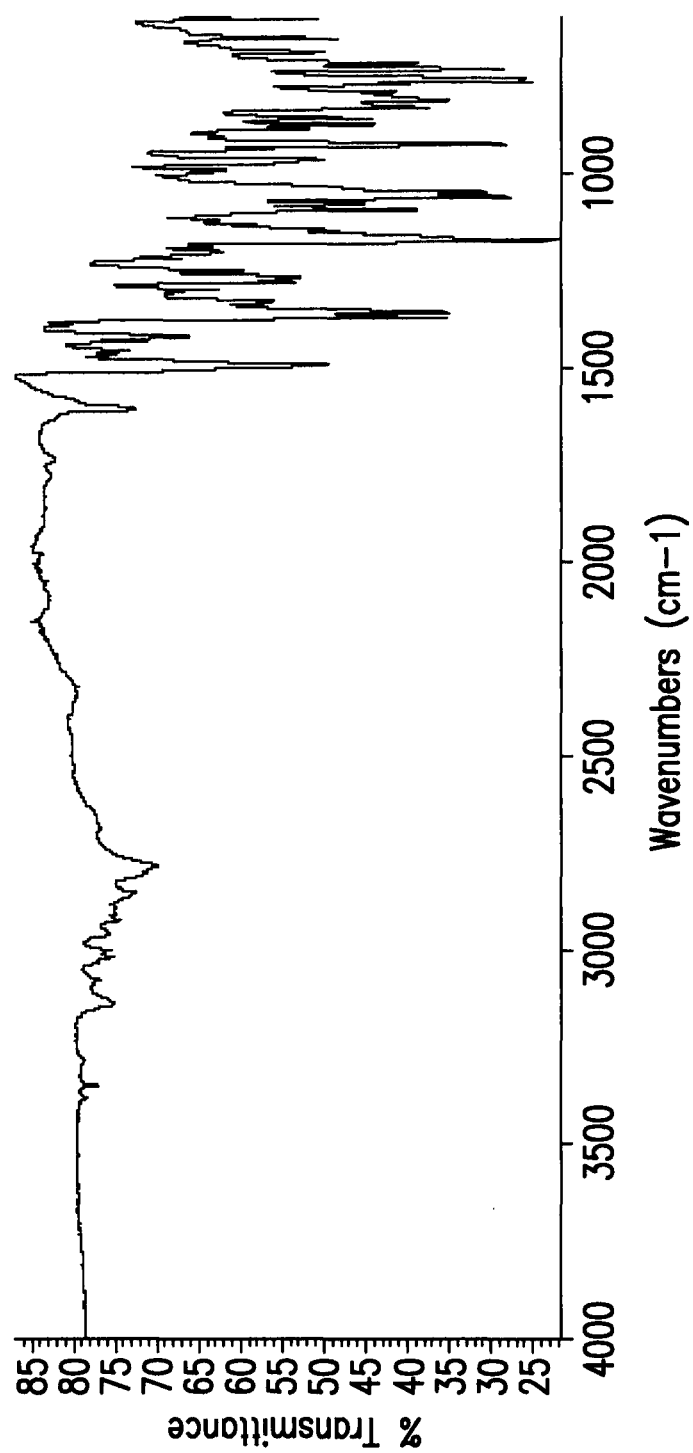
FIG. 5 is an IR spectra of crystalline Form II of Compound I.

FIG. 5 is an IR spectra of Form I of Compound I. Crystalline Form I can be further characterized by the IR spectra of FIG. 5.

Figure 10:
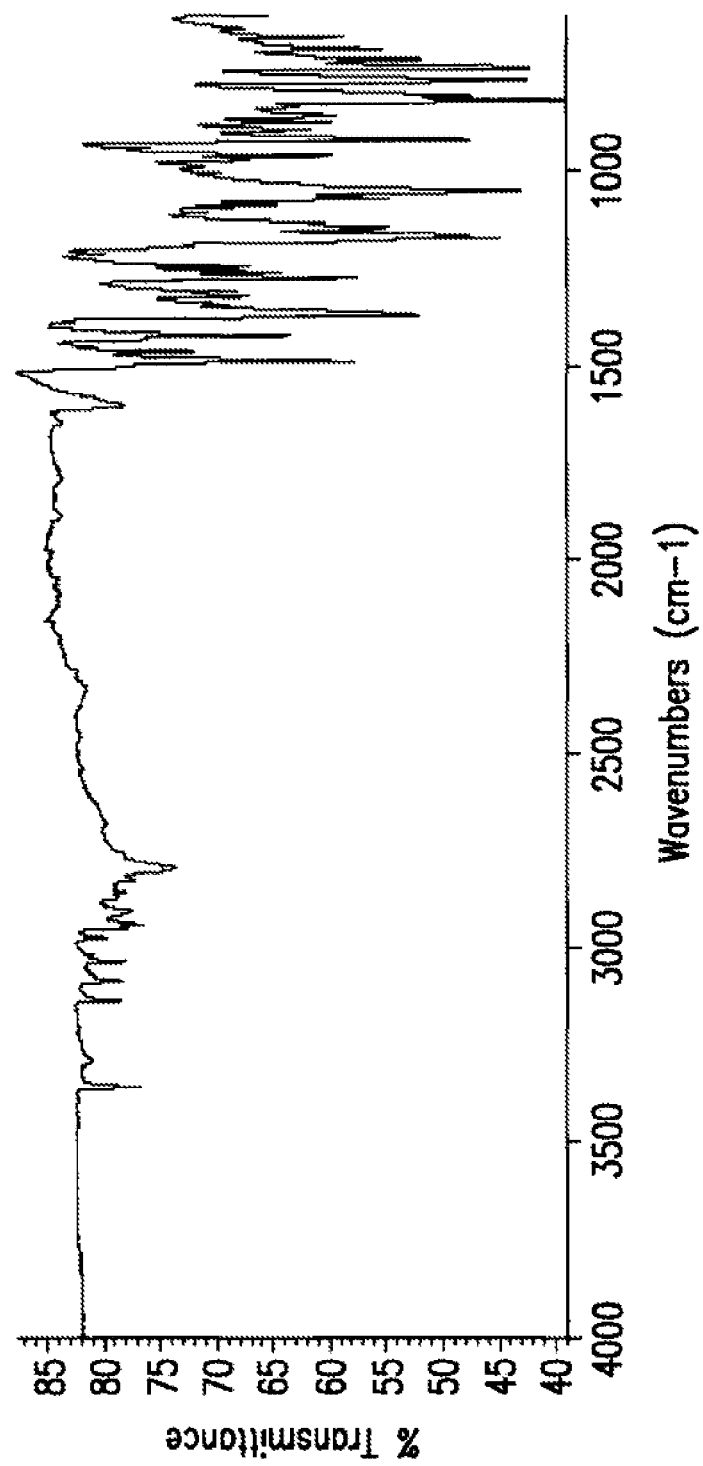
FIG. 10 is an IR spectra of crystalline Form II of Compound I.

FIG. 10 is an IR spectra of Form II of Compound I. Crystalline Form II can be further characterized by the IR spectra of FIG. 10.

In addition to the X-ray powder diffraction patterns described above, the crystalline forms of Compound I of the present invention were further characterized by means of their differential scanning calorimetry (DSC) curves and their thermogravimetric analysis (TGA) curves.

DSC

Differential Scanning calorimetry data were acquired using TA Instruments DSC 2910 or DSC2000. Between 2 and 6 mg sample was weighed into a pan and covered. This pan was then covered and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 250° C. The data was analyzed using Universal Analysis 2000 Version 3.9A. The thermal events were integrated between baseline temperature points that are above and below the temperature range over which the thermal event is observed. The data reported are the onset temperature, peak temperature and enthalpy.

Figure 3:
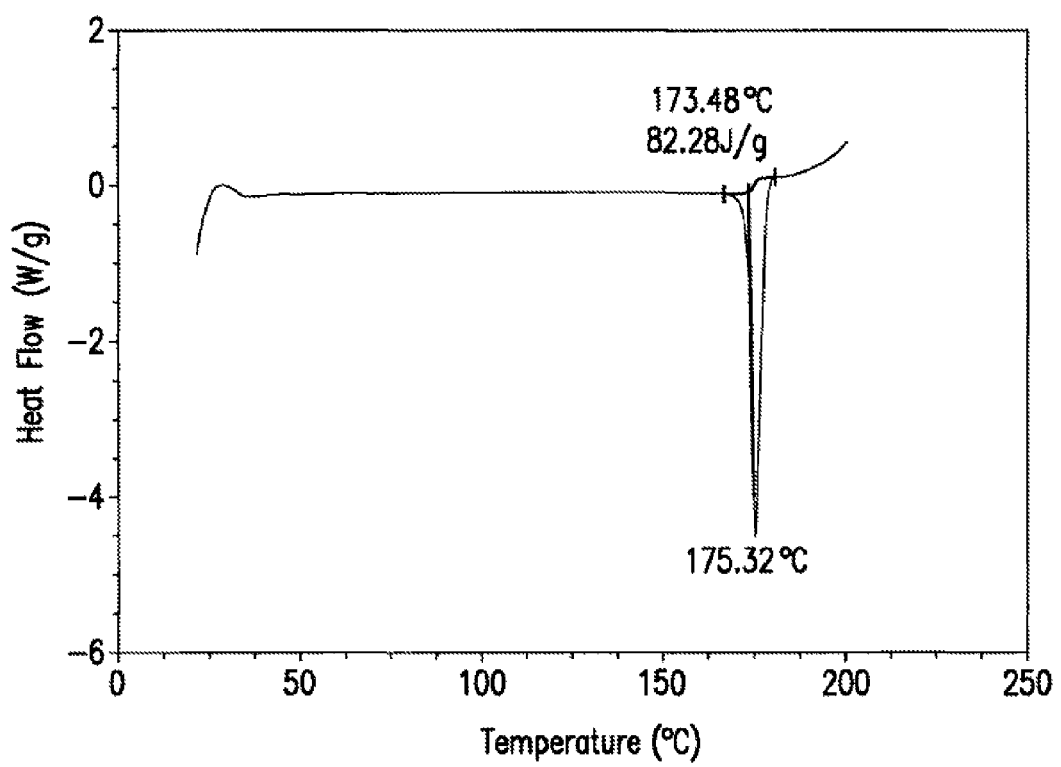
FIG. 3 is a differential scanning calorimetry (DSC) curve of crystalline Form I of Compound I.
Figure 8:
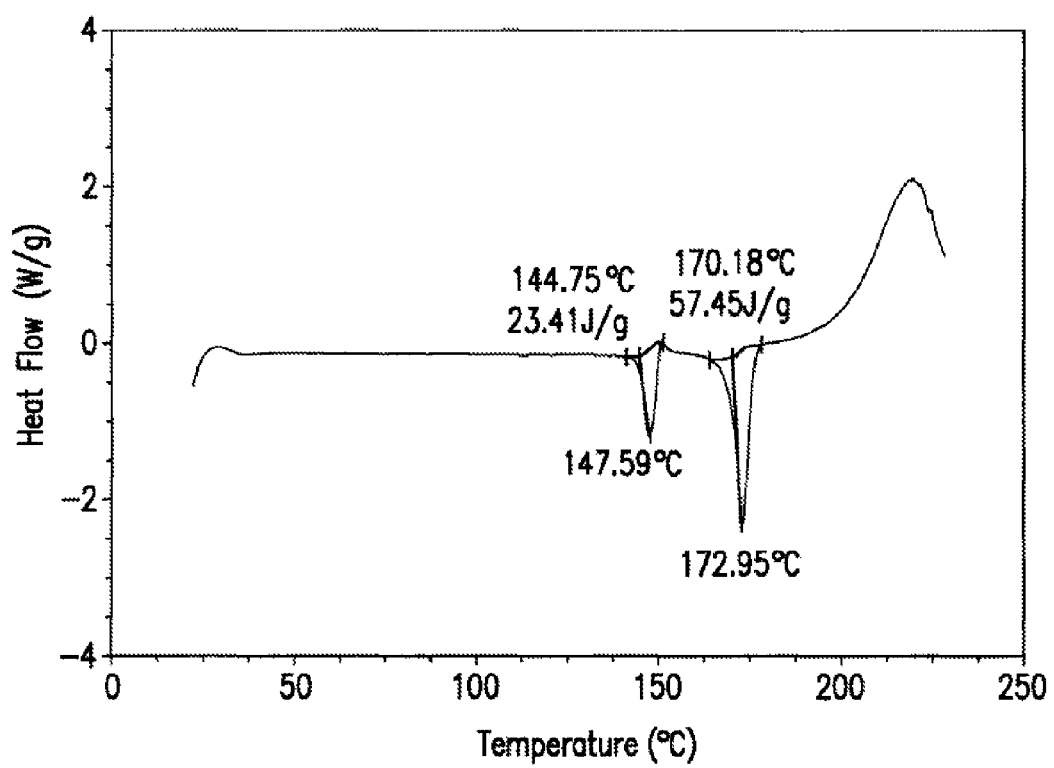
FIG. 8 is a differential scanning calorimetry (DSC) curve of crystalline Form II of Compound I.
Figure 13:
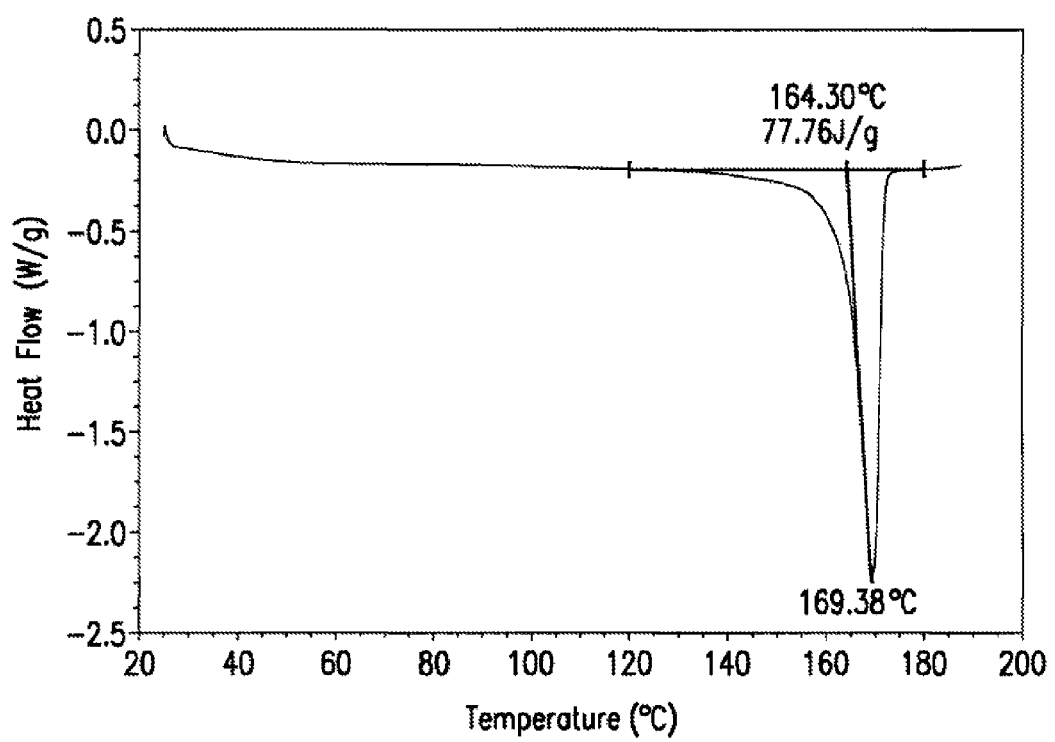
FIG. 13 is a differential scanning calorimetry (DSC) curve of crystalline Form III of Compound I.
Figure 16:
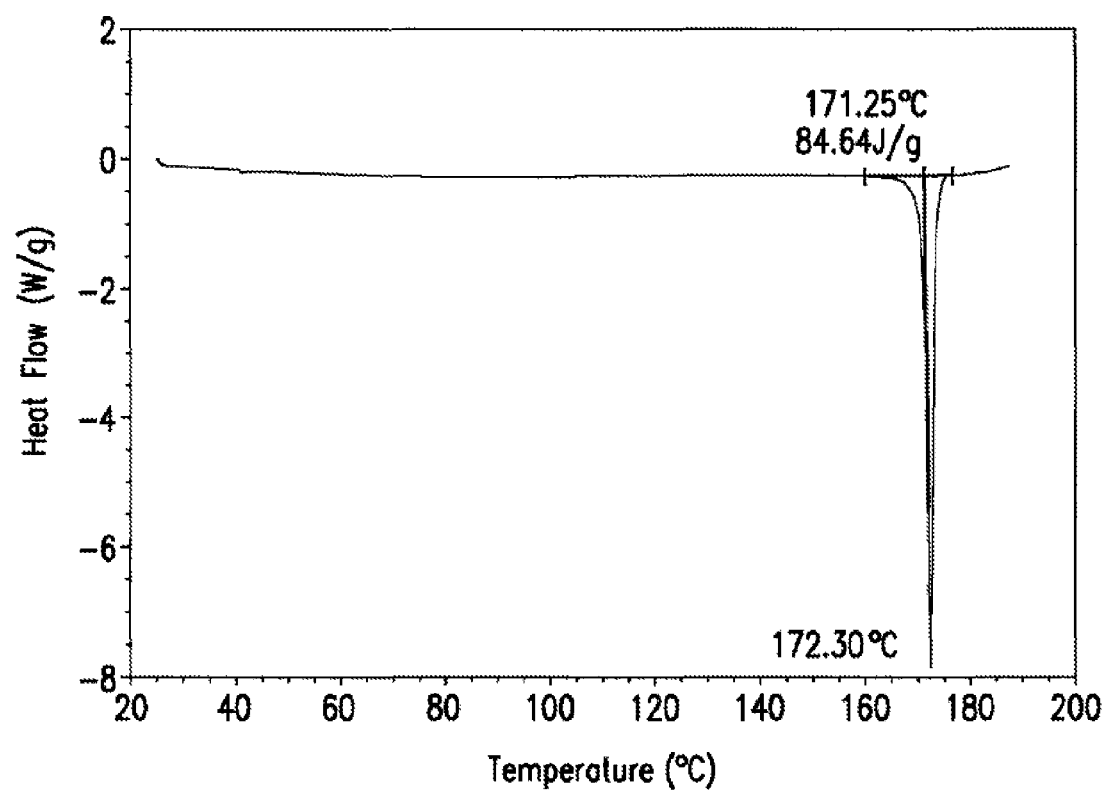
FIG. 16 is a differential scanning calorimetry (DSC) curve of crystalline Form IV of Compound I.

Crystalline Form I can be further characterized by the differential scanning calorimetric (DSC) curve of FIG. 3. Crystalline Form II can be further characterized by the differential scanning calorimetric (DSC) curve of FIG. 8. Crystalline Form III can be further characterized by the differential scanning calorimetric (DSC) curve of FIG. 13. Crystalline Form IV can be further characterized by the differential scanning calorimetric (DSC) curve of FIG. 16.

TGA

Figure 7:
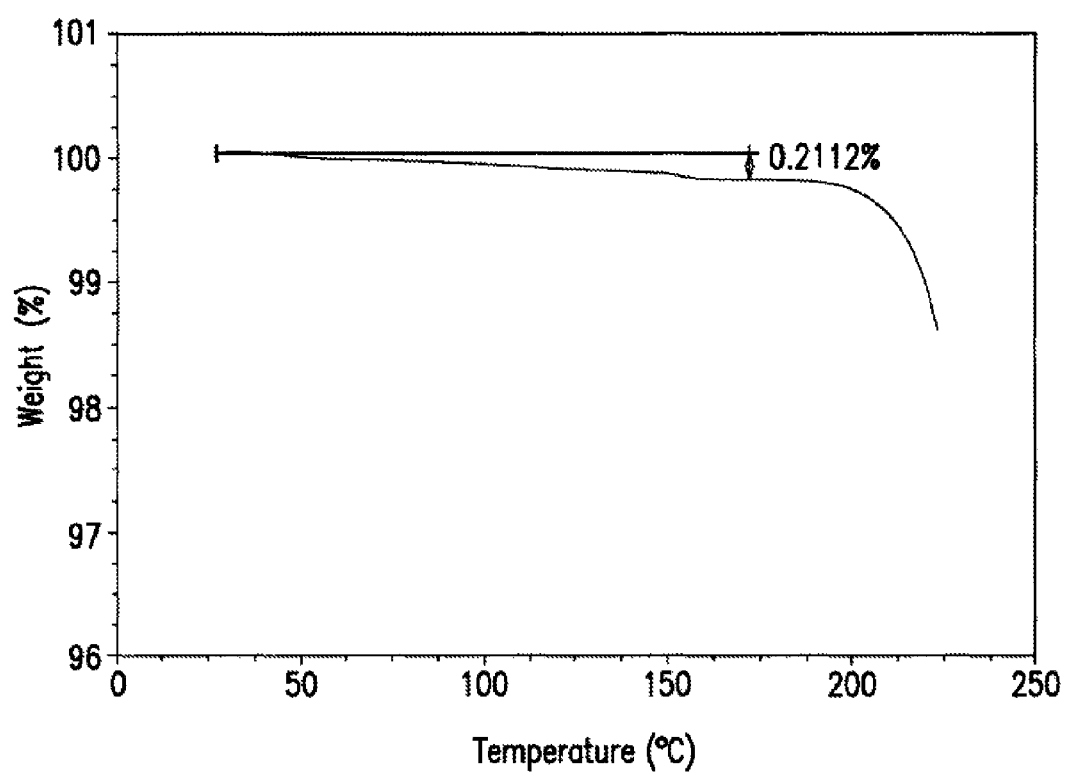
FIG. 7 is a thermogravimetric analysis (TGA) curve of crystalline Form II of Compound I.
Figure 12:
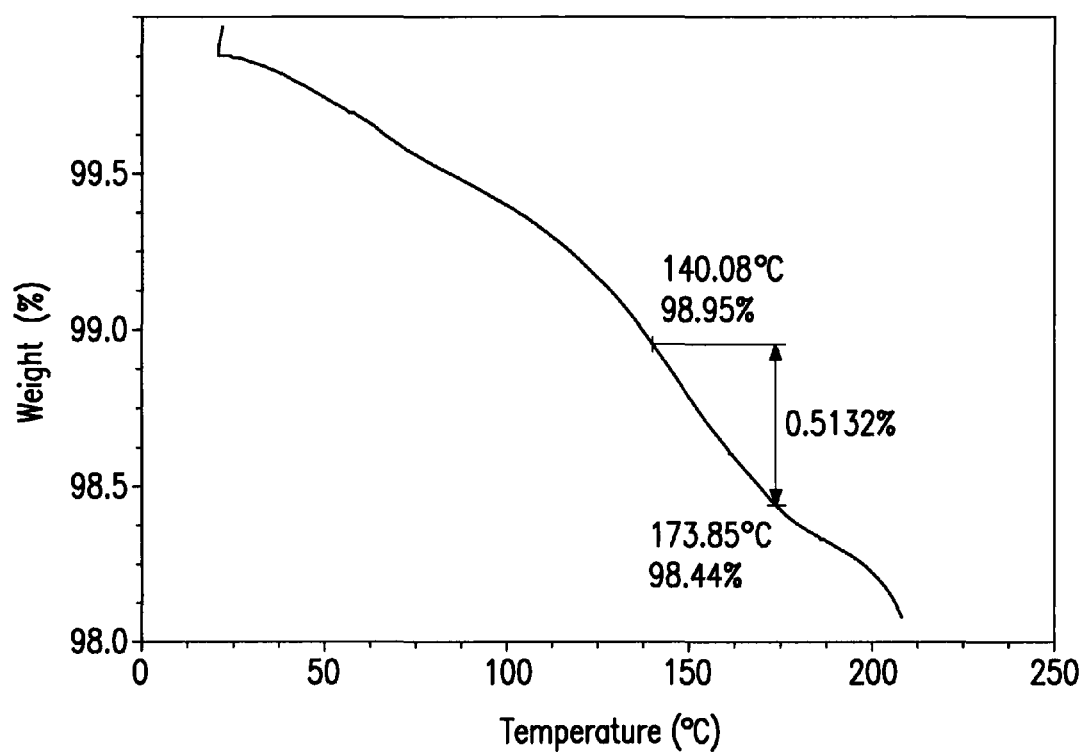
FIG. 12 is a thermogravimetric analysis (TGA) curve of crystalline Form III of Compound I.

Thermogravimetric data was acquired using a Perkin Elmer model TGA 7. Experiments were performed under a flow of nitrogen and using a heating rate of 10° C./min to a maximum temperature of approximately 250° C. After automatically taring the balance, 5 to 20 mg of sample was added to the platinum pan, the furnace was raised, and the heating program started. Weight/temperature data are collected automatically by the instrument. Analyses of the results were carried out by selecting the Delta Y function within the instrument software and choosing the temperatures between which the weight loss is to be calculated. Weight losses are reported up to the onset of decomposition/evaporation. Crystalline Form I can be further characterized by the thermogravimetric analysis (TGA) curve of FIG. 2. Crystalline Form II can be further characterized by the thermogravimetric analysis (TGA) curve of FIG. 7. Crystalline Form III can be further characterized by the thermogravimetric analysis (TGA) curve of FIG. 12. Crystalline Form IV can be further characterized by the thermogravimetric analysis (TGA) curve of FIG. 15.

Figure 2:
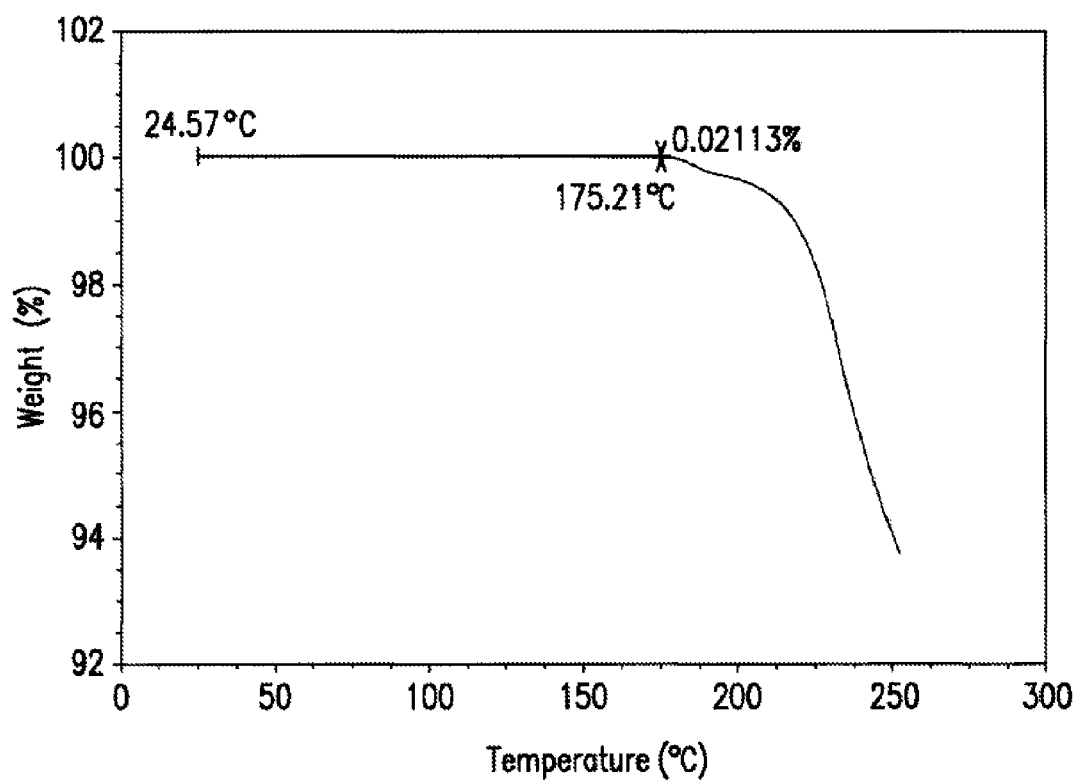
FIG. 2 is a thermogravimetric analysis (TGA) curve of crystalline Form I of Compound I.

A representative sample of Form I was analyzed by DSC and TGA according to the methods described above. Form I displays one endotherm (melting of Form I confirmed by hot stage microscopy) with Tonset=173.48° C., Tpeak=175.32° C., and ΔH=82.28 J/g (FIG. 3). Thermogravimetric analysis exhibits insignificant weight loss between room temperature and melting point of Form I (FIG. 2).

A representative sample of Form II was analyzed by DSC (FIG. 8) and TGA (FIG. 7) according to the methods described above. The first endotherm in the DSC curve is associated with the melting of Form II with $T_{onset}$=144.75° C., $T_{peak}$=147.59° C., and ΔH=23.41 J/g (FIG. 11). The first endotherm is followed by a recrystallization event to produce Form I at ~150° C. and finally by the melting of form I at $T_{onset}$=170.18° C., $T_{peak}$=172.95° C., and ΔH=57.45 J/g. TG analysis exhibits minimum weight loss (trapped solvent) between room temperature and melting of Form I.

DSC of Form III (FIG. 13) displays one endotherm associated with the melting of Form III with Tonset=164.30° C., Tpeak=169.38° C., and ΔH=23.41 J/g. Thermogravimetric analysis (FIG. 12) shows ~1% w/w residual solvent in the initial material which was removed by heating at 140 C and holding for 10 min.

Figure 15:
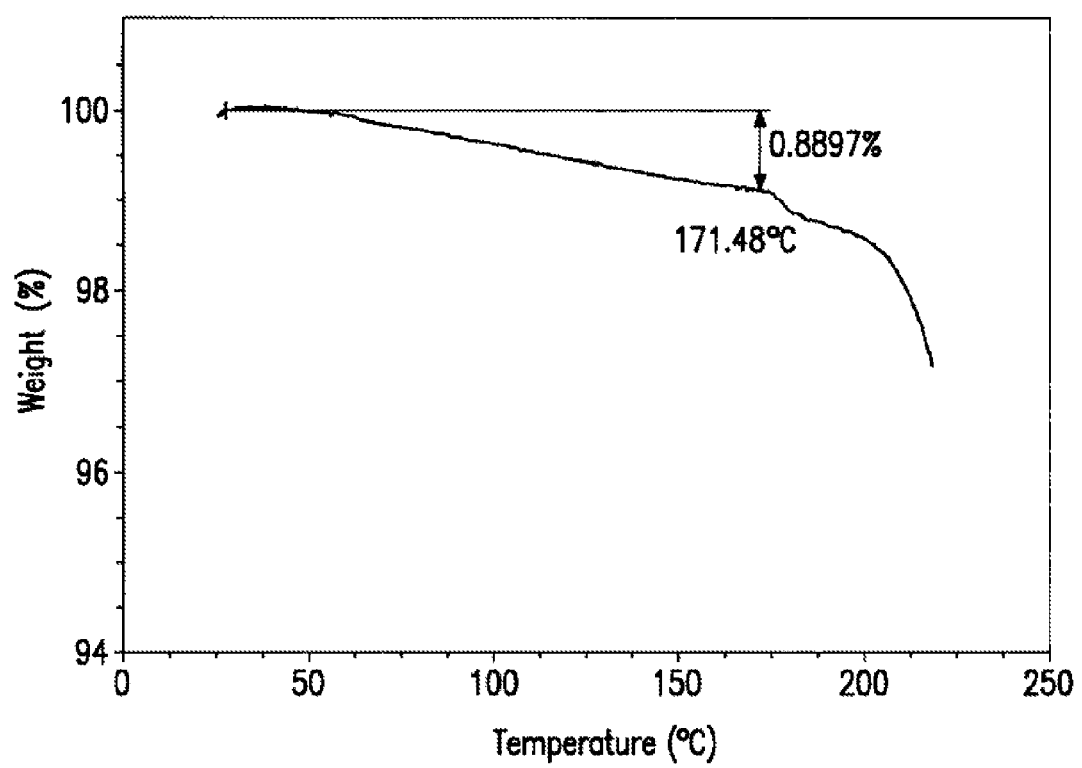
FIG. 15 is a thermogravimetric analysis (TGA) curve of crystalline Form IV of Compound I.

DSC of Form IV (FIG. 16) displays one endotherm associated with the melting of Form IV with Tonset=171.25° C., Tpeak=172.30° C., and ΔH=84.64 J/g. Less than 1% weight loss is observed up to melting using TGA (FIG. 15).

What is claimed is:

1. Crystalline (2R,3S,5R)-2-(2,5-Difluorophenyl)-5-[2-(methylsulfonyl)-2,6-dihydropyrrolo[3,4-c]pyrazol-5(41i)-yl]tetrahydro-2H-pyran-3-amine of Compound I:

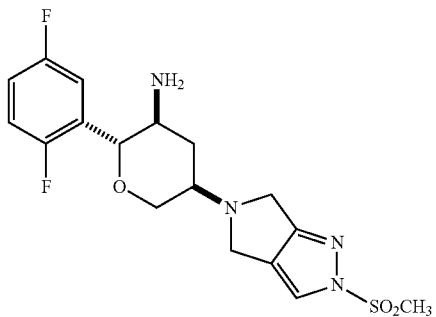

characterized by a solid-state carbon-13 nuclear magnetic resonance (NMR) spectra having chemical shifts at 163.6, 157.9, 128.9, 124.3 and 119.0 ppm.

2. The crystalline form of claim 1, characterized by a solid-state carbon-13 nuclear magnetic resonance (NMR) spectra having chemical shifts at 163.6, 157.9, 128.9, 124.3, 119.0, 90.1, 73.2, 59.9, 48.6 and 42.6 ppm.

3. The crystalline form of claim 1, further characterized by differential scanning calorimetric (DSC) thermogram which shows a maximum endothermal peak at or about 175.32° C.

4. The crystalline form of claim 1, further characterized by a thermogravimetric analysis (TGA) thermogram characterized by insignificant weightloss between room temperature and melting point.

5. Crystalline (2R,3S,5R)-2-(2,5-Difluorophenyl)-5-[2-(methylsulfonyl)-2,6-dihydropyrrolo[3,4-c]pyrazol-5(41i)-yl]tetrahydro-2H-pyran-3-amine of Compound I:

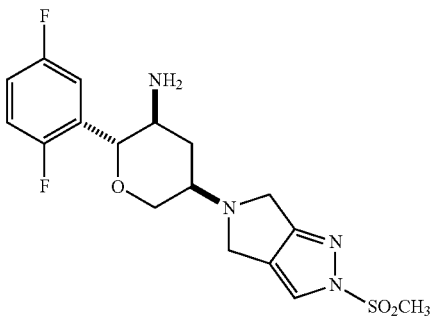

characterized by a solid-state carbon-13 nuclear magnetic resonance (NMR) spectra having chemical shifts at 132.1, 127.5, 116.9, 73.5 and 42.2 ppm.

6. The crystalline form of claim 5, characterized by a solid-state carbon-13 nuclear magnetic resonance (NMR) spectra having chemical shifts at 132.1, 127.5, 116.9, 79.0, 73.5, 62.3, 56.3, 53.0 and 42.2 ppm.

7. The crystalline form of claim 5, further characterized by the differential scanning calorimetric (DSC) thermogram which shows an endothermal peak at or about 172.95° C.

8. Crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine of Compound I:

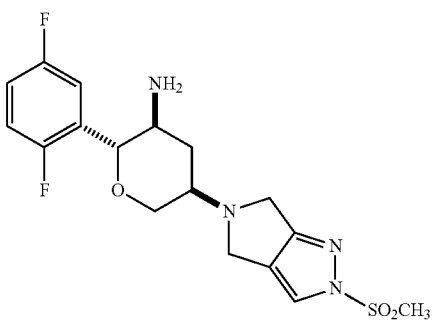

characterized by having at least four peaks in its powder X-ray diffraction pattern selected from the group consisting of 14.5 +0.1 2θ, 15.9 +0.1 2θ, 17.3 +0.1 2θ, 18.7 +0.1 2θ, 19.5 +0.1 2θ, 21.2 +0.1 2θ, 22.0 +0.1 2θ and 23.2 +0.1 2θ and further characterized by differential scanning calorimetric (DSC) thermogram which shows an endothermal peak at or about 169.38° C.

9. Crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine of Compound I:

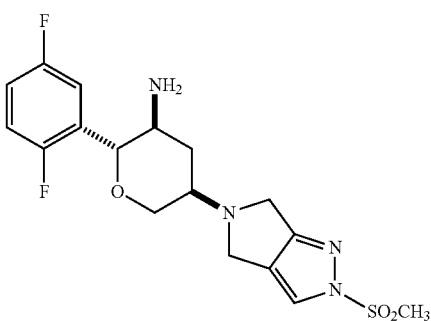

characterized by having at least four peaks in its powder X-ray diffraction pattern selected from the group consisting of 8.1 +0.1 2θ, 10.6 +0.1 2θ, 16.0 +0.1 2θ, 16.9 +0.1 2θ, 19.5 +0.1 2θ, 21.3 +0.1 2θ, 23.3 +0.1 2θ and 25.4 +0.1 2θ and further characterized by differential scanning calorimetric (DSC) thermogram which shows an endothermal peak at or about 172.30° C.

10. A method of treating Type 2 diabetes comprising administering to a mammal in need of such treatment a therapeutically effective amount of a crystalline form according to claim 1.

11. A pharmaceutical composition comprising a drug substance that comprises crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine of claim 1 and a pharmaceutically acceptable carrier.

12. A method of treating Type 2 diabetes comprising administering to a mammal in need of such treatment a therapeutically effective amount of a crystalline form according to claim 2.

13. A pharmaceutical composition comprising a drug substance that comprises crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine of claim 2 and a pharmaceutically acceptable carrier.

* * * * *